United States Patent
Prata et al.

(10) Patent No.: US 11,339,236 B2
(45) Date of Patent: May 24, 2022

(54) POLYMERIC THICKENER FOR IRIDESCENT LIQUID HAND SOAP COMPOSITIONS

(71) Applicant: Lubrizol Advanced Materials, Inc., Cleveland, OH (US)

(72) Inventors: Joseph E. Prata, North Royalton, OH (US); Michael P. Myers, Barberton, OH (US); Krishnan Tamareselvy, Somerset, NJ (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 98 days.

(21) Appl. No.: 16/651,429

(22) PCT Filed: Sep. 19, 2018

(86) PCT No.: PCT/US2018/051670
§ 371 (c)(1),
(2) Date: Mar. 27, 2020

(87) PCT Pub. No.: WO2019/067279
PCT Pub. Date: Apr. 4, 2019

(65) Prior Publication Data
US 2020/0299439 A1  Sep. 24, 2020

Related U.S. Application Data

(60) Provisional application No. 62/564,569, filed on Sep. 28, 2017.

(51) Int. Cl.
| | | |
|---|---|---|
| *C11D 3/00* | (2006.01) | |
| *C11D 3/37* | (2006.01) | |
| *C11D 17/00* | (2006.01) | |
| *C08F 220/06* | (2006.01) | |
| *C08F 220/18* | (2006.01) | |
| *A61K 8/81* | (2006.01) | |
| *A61Q 5/02* | (2006.01) | |
| *A61Q 19/10* | (2006.01) | |
| *C08F 2/00* | (2006.01) | |
| *C08F 2/22* | (2006.01) | |
| *C08K 5/00* | (2006.01) | |

(52) U.S. Cl.
CPC .......... *C08F 220/06* (2013.01); *A61K 8/8152* (2013.01); *A61Q 5/02* (2013.01); *A61Q 19/10* (2013.01); *C08F 2/001* (2013.01); *C08F 2/22* (2013.01); *C08F 220/1802* (2020.02); *C08F 220/1804* (2020.02); *C08K 5/0025* (2013.01); *C11D 3/3765* (2013.01); *A61K 2800/48* (2013.01); *A61K 2800/596* (2013.01); *A61K 2800/654* (2013.01)

(58) Field of Classification Search
None
See application file for complete search history.

(56) References Cited

U.S. PATENT DOCUMENTS

2015/0342858 A1* 12/2015 Tamareselvy ........ A61K 8/8158
424/70.12

FOREIGN PATENT DOCUMENTS

| WO | 2012/006402 A1 | 1/2012 |
| WO | 2012/044929 A2 | 4/2012 |
| WO | 2012/047957 A1 | 4/2012 |
| WO | 2014/099512 A2 | 6/2014 |
| WO | 2016/106167 A1 | 6/2016 |

* cited by examiner

*Primary Examiner* — Brian Gulledge
(74) *Attorney, Agent, or Firm* — Thoburn Dunlap

(57) ABSTRACT

Disclosed are multi-staged acrylic emulsion polymers and their use as rheology modifiers in the formulation of liquid personal care cleansers for the skin and hair. More particularly, the present technology relates to liquid cleansing compositions that possess the necessary rheology properties to stably suspend particles and insoluble materials within the cleanser but may also be used with pump dispensers to generate and dispense a creamy foam without fouling the pump mechanism.

23 Claims, No Drawings

POLYMERIC THICKENER FOR IRIDESCENT LIQUID HAND SOAP COMPOSITIONS

CROSS REFERENCE TO RELATED APPLICATION

This application claims priority from PCT Application Serial No. PCT/US2018/051670 filed on Sep. 19, 2018, which claims the benefit of U.S. Provisional Application No. 62/564,569 filed on Sep. 28, 2017, both of which are incorporated in their entirety by reference herein.

FIELD OF THE PRESENT TECHNOLOGY

The present technology relates to multi-staged acrylic polymers and their use as rheology modifiers in the formulation of liquid personal care cleansers for the skin and hair. More particularly, the present technology relates to liquid cleansing compositions that possess the necessary rheology properties to stably suspend particles and insoluble materials within the cleanser but may also be used with pump dispensers to generate and dispense a creamy foam.

BACKGROUND

Liquid personal care cleansing products such as liquid hand soaps containing suspended particulate and insoluble materials are known in the art. Particulate materials are often formulated into liquid hand soap compositions for the delivery of actives and/or to give the product an aesthetic visual appeal, including soaps formulated with iridescent materials such as mica, polypropylene beads, cosmetic glitters, ethylene glycol distearate and other materials which deliver a desirable aesthetic visual effect. In conventional liquid hand soaps containing these materials it is typically necessary to formulate the composition with a polymeric thickener to provide a viscous rheology. Frequently, acrylic based polymers are employed as thickeners as they provide the essential rheology required to prevent settling or other physical instability in the product during production, shipping, storage and use. However, this viscous consistency is not a preferred rheology for a liquid foamable hand soap because of problems of product dispensing and undesirable aesthetics as these polymers tend to form films as they dry.

In recent marketing trends it has been desirable for liquid cleansing compositions to be foamable. Foaming hand soaps are increasingly preferred by the consumer as foams tend to be much easier to spread than the corresponding liquid and there is much less waste due to splashing and run-off since foams have much higher surface tensions than the liquid. Moreover, consumers often associate foaming cleansers with a better cleansing effect, and a perception that the cleanser is "working" better than a non-foaming cleanser. Consequently, it is advantageous for a cleanser to be capable of producing voluminous foam when used in connection with a dispenser, such as a pump foam dispenser. A pump foam dispenser contains a single or multiple fine mesh screens which shear the surfactant solution to form a rich creamy foam as the soap is dispensed.

However, delivery of liquid cleansing compositions through foam producing dispensers has presented many challenges. As discussed previously, it is often desirable for cleansers to include additives such as skin or hair benefit active agents as well as iridescent materials for visual appeal, in addition to cleansing surfactants. However, such additives can interfere with the ability of the composition to foam. Furthermore, certain types of foam producing dispensers that use porous filters or meshed screens which shear the surfactant solution to produce the foam may not work well (or at all) with even moderately viscous compositions. Consequently, foamable cleansing compositions currently on the market are water-thin to be easily pumped through shear producing porous filters or mesh screens located in the pump head. These water-thin cleansers are incapable of stably suspending particulate additives evenly throughout the cleanser and still produce the volume of foam desired by consumers. Moreover, the conventionally employed acrylic based thickeners tend to form gels and films upon exposure to the ambient environment, causing clogging of the pump and/or product misdirection as the soap is dispensed from the container due to the build-up of gelled or semi-dried thickener component located in or around the outer orifice of the pump dispenser. An additional drawback of some of these conventional thickeners is that they impart a hazy appearance when formulated with cleansing surfactants which detracts from the desired iridescent appearance of the contained product.

A rheology modifying polymer with low thickening efficiency, poor film forming attributes, high suspending properties and which does not deleteriously affect a clear product appearance is desirable in the formulation of a new pumpable foaming cleansing product for the personal care marketplace.

SUMMARY OF THE DISCLOSED TECHNOLOGY

The disclosed technology relates to stable personal care cleansing compositions comprising a structured acrylic polymeric rheology modifier, a foamable cleansing surfactant and, optionally, a particulate material(s) requiring long term suspension or stabilization that is insoluble in the aqueous based surfactant containing composition.

A further aspect of the disclosed technology relates to clear, rheologically and phase stable cleansing compositions formulated at relatively low viscosities to maintain pumpability and foamability and can suspend particulate and/or insoluble materials compared to the prior art polymeric thickeners.

A further aspect of the disclosed technology relates to a rheology modifying polymer with low thickening efficiency, poor film forming attributes, high suspending properties and which does not deleteriously effect product clarity when formulated in an aqueous surfactant containing cleansing composition.

A further aspect of the disclosed technology relates to a rheology modifying polymer for liquid soap compositions which facilitates the stable suspension of iridescent materials, a pumpable viscosity and does not occlude (drying or sticking) the pump head during the product lifetime (until the product container is emptied).

A further aspect of the disclosed technology relates to staged polymer particles comprising, or consisting of, or consisting essentially of:

(a) about 15 percent by weight of a first stage polymeric core which is polymerized from a monomer mixture comprising: (i) from about 53 to about 60 weight percent of at least one ethylenically unsaturated $C_3$-$C_6$ carboxylic acid monomer, (ii) from about 39 to about 46; weight percent of at least one $C_1$-$C_4$ alkyl (meth)acrylate monomer, and (iii) at least one crosslinking monomer; (b) about 85 percent by weight of a second stage polymeric shell which is polymerized from a monomer mixture comprising: (i) from about 47 to about 55 weight percent of at least one ethylenically unsaturated $C_3$-$C_6$ carboxylic acid monomer, (ii) from about 52 to about 44 weight percent of at least one $C_1$-$C_4$ alkyl (meth)acrylate monomer, and (iii) at least one crosslinking monomer; wherein the weight fraction of the at least one $C_3$-$C_6$ carboxylic acid monomer present in said first stage monomer mixture is 3 to 20 percent greater than the weight fraction of at least one $C_3$-$C_6$ carboxylic acid monomer present in said second stage monomer mixture; and wherein the sum total of said crosslinking monomer present in said first and in said second stage monomer mixtures ranges from about 0.5 weight percent to about 1.5 weight percent (based on the weight of the total monomer present in said first and second stage monomer mixtures) and the weight fraction of said crosslinking monomer present in said first stage monomer mixture to said second stage monomer mixture ranges from 15:50 to 85:50.

DESCRIPTION OF EXEMPLARY EMBODIMENTS

As used herein and throughout the specification, the term "staged polymer particle" means a polymer particle prepared by a sequential or a staged emulsion polymerization process wherein a first stage monomer mixture is polymerized to completion or near completion to yield a first stage polymer (core) followed by polymerizing a second stage monomer mixture in the presence of the first stage polymer to yield a second stage polymer (shell). Without being bound to any particular theory, it is theorized that the first stage polymer segment is bonded to and/or associated with the second stage polymer segment by covalent bonding or by hydrogen bonding or by physical entanglement of the first and second polymer segments or by a combination of anyone of the foregoing bonding mechanisms.

As used herein the term "ambient room temperature (RT)" refers to a temperature ranging from about 20 to about 25° C.

As used herein the term "optically clear" refers to compositions of the present technology having turbidity value that is equal to or less than about 52 NTU, equal to or less than about 50 NTU, equal to or less than about 40 NTU, equal to or less than about 30 NTU, equal to or less than about 20 NTU as measured by the Turbidity Test described in the test protocol below (a lower NTU value relates to a composition that is clearer than a composition having a higher NTU value).

As used herein, the prefix "(meth)acryl" includes "acryl" as well as "methacryl". For example, the term "(meth) acrylic acid" includes both acrylic acid and methacrylic acid.

Unless otherwise stated, all percentages, parts, and ratios expressed herein are based upon the total weight of the components/monomers contained in the compositions/copolymers of the disclosed technology.

While overlapping weight ranges for the various components, ingredients, and monomers that can be contained in the compositions or copolymers have been expressed for selected embodiments and aspects of the disclosed technology, it should be readily apparent that the specific amount of each component in the disclosed compositions/copolymers will be selected from its disclosed range such that the amount of each component/monomer is adjusted such that the sum of all components/monomers in the composition/copolymer will total 100 weight percent. The amounts employed will vary with the purpose and character of the desired product and can be readily determined by one skilled in the art.

The foamable soap compositions containing the staged emulsion polymer of the disclosed technology may suitably comprise, consist essentially of, or consist of, the components, elements, and process delineations described herein. The disclosed technology illustratively disclosed herein suitably may be practiced in the absence of any element which is not specifically disclosed herein.

First Stage Polymer Components

The first stage polymer segment is a crosslinked acrylic copolymer that is prepared from a monomer mixture comprising, or consisting of, or consisting essentially of (i) from about 53 to about 60 wt. % in one aspect, from about 53.5 to about 58 wt. % in another aspect, and from about 54 to about 56 wt. % in a still further aspect of at least one ethylenically unsaturated $C_3$-$C_6$ carboxylic acid containing monomer; (ii) from about 39 to about 46 wt. % in one aspect, from about 41 to about 45.5 wt. % in another aspect, and from about 43 to about 45 wt. % in a still further aspect of at least one $C_1$-$C_4$ alkyl (meth)acrylate monomer; and (iii) at least one crosslinking monomer.

Exemplary ethylenically unsaturated $C_3$-$C_6$ carboxylic acid monomers include acrylic acid, methacrylic acid, itaconic acid, citraconic acid, maleic acid, maleic anhydride, fumaric acid, crotonic acid, aconitic acid, and mixtures thereof.

Exemplary $C_1$-$C_4$ alkyl (meth)acrylate monomers include methyl acrylate, methyl methacrylate, ethyl acrylate, ethyl methacrylate, n-butyl acrylate, n-butyl methacrylate, t-butyl acrylate, t-butyl methacrylate, and mixtures thereof.

Second Stage Polymer Components

The second stage polymer segment is a crosslinked acrylic copolymer that is prepared from a monomer mixture comprising, or consisting of, or consisting essentially of (i) from about 47 to about 55 wt. % in one aspect, from about 48 to about 53 wt. % in another aspect, and from about 49 to about 50 wt. % in a still further aspect of at least one ethylenically unsaturated $C_3$-$C_6$ carboxylic acid containing monomer; (ii) from about 52 to 44 wt. % in one aspect, from about 51 to about 46 wt. % in another aspect, and from about 50 to about 49 wt. % in a still further aspect of at least one $C_1$-$C_4$ alkyl (meth)acrylate monomer; and (iii) at least one crosslinking monomer.

The relative amount of the at least one ethylenically unsaturated $C_3$-$C_6$ carboxylic acid containing monomer present in the first stage monomer mixture is from about 3 to about 20 wt. % greater than the at least one ethylenically unsaturated monomer present in the second stage monomer mixture.

Crosslinking Monomer

The crosslinking monomer used to crosslink the first stage polymer segment and the second stage polymer segment can be the same or different. The crosslinking monomer is an ethylenically polyunsaturated compound containing at least two ethylenically unsaturated moieties. Exemplary polyunsaturated compounds include di(meth)acrylate compounds such as ethylene glycol di(meth)acrylate, polyethylene glycol di(meth)acrylate, triethylene glycol di(meth)acrylate, 1,3-butylene glycol di(meth)acrylate, 1,6-butylene glycol di(meth)acrylate, 1,6-hexanediol di(meth)acrylate, neopentyl glycol di(meth)acrylate, 1,9-nonanediol di(meth)acrylate, 2,2'-bis(4-(acryloxy-propyloxyphenyl)propane, 2,2'-bis(4-(acryloxydiethoxy-phenyl)propane, and zinc acrylate (i.e., $2(C_3H_3O_2)Zn^{++}$); tri(meth)acrylate compounds such as, trimethylolpropane tri(meth)acrylate, trimethylolethane tri(meth)acrylate, and tetramethylolmethane tri(meth)acrylate; tetra(meth)acrylate compounds such as ditrimethylolpropane tetra(meth)acrylate, tetramethylolmethane tetra(m- eth)acrylate, and pentaerythritol tetra(meth)acrylate; hexa (meth)acrylate compounds such as dipentaerythritol hexa (meth)acrylate; allyl compounds such as allyl (meth) acrylate, diallylphthalate, diallyl itaconate, diallyl fumarate, and diallyl maleate; polyallyl ethers of sucrose having from 2 to 8 allyl groups per molecule, polyallyl ethers of pentaerythritol such as pentaerythritol diallyl ether, pentaerythritol triallyl ether, and pentaerythritol tetraallyl ether; polyallyl ethers of trimethylolpropane such as trimethylolpropane diallyl ether and trimethylolpropane triallyl ether. Other suitable polyunsaturated compounds include divinyl glycol, divinyl benzene, and methylenebisacrylamide.

The total amount of crosslinking monomer component utilized in the first and second stage monomer mixtures ranges from 0.5 wt. % to about 1.5 wt. % based on the wt. of total monomer in the first and second stage monomer mixtures, wherein the weight fraction of the crosslinking monomer(s) in the first stage monomer mixture to the weight fraction of the crosslinking monomer(s) in the second stage monomer mixture ranges from 15:50 to 85:50.

Optionally, a chain transfer agent can be added to the first and second stage monomer mixtures. Exemplary chain transfer agents include, but are not limited to, thio- and disulfide containing compounds, such as $C_1$-$C_{18}$ alkyl mercaptans, mercaptocarboxylic acids, mercaptocarboxylic esters, thioesters, $C_1$-$C_{18}$ alkyl disulfides, aryldisulfides, polyfunctional thiols such as trimethylolpropane-tris-(3-mercaptopropionate), pentaerythritol-tetra-(3-mercaptopropionate), pentaerythritol-tetra-(thioglycolate), and pentaerythritol-tetra-(thiolactate), dipentaerythritol-hexa-(thioglycolate), and the like; phosphites and hypophosphites; haloalkyl compounds, such as carbon tetrachloride, bromotrichloromethane, and the like; and catalytic chain transfer agents such as, for example, cobalt complexes (e.g., cobalt (II) chelates).

In one aspect of the present technology, the chain transfer agent is selected from octyl mercaptan, n-dodecyl mercaptan (n-DDM), t-dodecyl mercaptan (t-DDM), hexadecyl mercaptan, octadecyl mercaptan (ODM), isooctyl 3-mercaptopropionate (IMP), butyl 3-mercaptopropionate, 3-mercaptopropionic acid, butyl thioglycolate, isooctyl thioglycolate, and dodecyl thioglycolate.

In one aspect, the chain transfer agent is utilized in an amount ranging from about 0 or 0.05 to about 1 wt. %, from about 0.1 to about 0.75 wt. %, from about 0.3 to about 0.5 wt. % (based on 100 wt. parts of monomer).

In one aspect, the staged polymer particles comprise, or consist of, or consist essentially of about 15 wt. %, or about 20 wt. %, or about 25 wt. % of the first stage polymer segment prepared from the first monomer mixture and about 85 wt. %, or about 80 wt. %, or about 75 wt. % of the second stage polymer segment prepared from the second monomer mixture.

In one aspect, the rheology modifier component of the present technology is a staged emulsion polymer comprising, or consisting of, or consisting essentially of:

(a) about 20 wt. % of a first stage polymer segment comprising, or consisting of, or consisting essentially of: (i) from about 53 to about 60 wt. % in one aspect, from about 53.5 to about 58 wt. % in another aspect, and from about 54 to about 56 wt. % in a still further aspect of polymerized residues of methacrylic acid; (ii) from about 39 to about 46 wt. % in one aspect, from about 45.5 to about 41 wt. % in another aspect, and from about 43 to about 45 wt. % in a still further aspect of ethyl acrylate; and (iii) at least one crosslinking monomer selected from trimethylolpropane triacrylate (TMPTA), triethylene glycol dimethacrylate (TEGDMA), trimethylolpropane diallyl ether (TMPDAE) and allyl pentaerythritol (APE), as well as mixtures thereof. Allyl pentaerythritol comprises a mixture of diallyl-, triallyl-, and tetraallyl ether adducts of pentaerythritol, with a majority (about 70-85 wt. %) of the mixture comprising the triallyl ether adduct.

(b) about 80 wt. % of a second stage polymeric segment comprising, or consisting of, or consisting essentially of: (i) from about 47 to about 55 weight percent of at least one ethylenically unsaturated $C_3$-$C_6$ carboxylic acid monomer, (ii) from about 52 to about 44 weight percent of polymerized residues of ethyl acrylate; and (iii) at least one crosslinking monomer selected from TMPTA, TEGDMA, TMPDAE and APE, wherein the weight fraction of the methacrylic acid residues present in said first stage polymer segment is 3 to 20 percent greater than the weight fraction of methacrylic acid residues present in said second stage polymer segment; and wherein the weight fraction of the crosslinking monomer residues in the first stage polymer segment to the weight fraction of the crosslinking monomer residues in the second stage polymer segment ranges from 15:50 to 85:50.

Without being bound to any particular theory, it is postulated that the greater amount of the carboxylic acid containing residues present in the first stage polymer segment compared to the second stage polymer segment, as well as a greater crosslink density in the second stage polymer segment compared to the first stage polymer segment leads to a "brittle" polymer that is less tacky. Increased polymer brittleness produces less tacky plugs at the dispenser orifice, allowing the dispenser to clear easily during normal use, thus preventing polymer obstruction of the dispenser to the point of failure (complete obstruction) or misdirected product as the soap leaves the dispenser orifice (partial obstruction).

In certain embodiments of the present technology, the polymeric rheology modifier component (based on 100% active solids) can be utilized in a foamable soap composition in an amount ranging from about 0.5 to about 5 wt. % in one aspect, from about 1 to about 3.0 wt. % in another aspect and from about 1.2 to about 2 wt. % in a further aspect (based on the total wt. of the composition).

In certain embodiments of the present technology, the neat polymer emulsion component has a minimum film formation temperature (MFFT) ranging from about 18 to about 40° C. in one aspect, from about 20 to about 35° C. in another aspect, from about 21 to about 30° C. in a further aspect, and from about 24 to about 26° C. in a still further aspect.

Staged Polymer Preparation

The staged polymer component of the disclosed technology comprises, or consists of, or consists essentially of at least two polymeric stages synthesized sequentially via staged free radical emulsion polymerization techniques. The staged polymer component of the disclosed technology comprises, or consists of, or consists essentially of a first stage polymer segment and a second stage polymer segment.

The first stage polymer segment is synthesized in a first stage emulsion polymerization reaction from a monomer mixture emulsified in a continuous aqueous phase comprising, or consisting of, or consisting essentially of a mixture of the first stage monomers set forth in the ranges disclosed above. The emulsified first stage monomers are polymerized in the presence of a suitable free radical forming initiator forming an emulsion of first stage polymeric particles. The second stage polymer segment is formed sequentially to the first stage polymer segment in a second emulsion polymerization stage. In the second polymerization stage, the second stage polymer segment is synthesized in a second stage emulsion polymerization reaction from a monomer mixture emulsified in a continuous aqueous phase comprising, or consisting of, or consisting essentially of a mixture of the second stage monomers set forth in the ranges disclosed above. The second stage polymer segment is prepared in the presence of the previously prepared first stage latex of the core stage polymer and additional free radical forming initiator. The end-product is a two-stage polymer or polymer composition comprising, or consisting of, or consisting essentially of a first stage polymer segment and a second stage polymer segment. The first stage polymer segment is richer in residues derived from the at least one ethylenically unsaturated $C_3$-$C_6$ carboxylic acid monomer (e.g., methacrylic acid) and lower in crosslink density than the second stage polymer segment. Conversely, the second stage polymer segment is richer in residues derived from the at least one $C_1$-$C_4$ alkyl (meth)acrylate monomer (e.g., ethyl acrylate) and higher in crosslink density than the first stage polymer segment.

Each segment of the staged polymer of the disclosed technology can be prepared from a monomer mixture containing one or more of the previously disclosed chain transfer agents. The chain transfer agent can be utilized to tailor the molecular weight of the staged polymer segments.

The emulsion polymerization of each stage can be carried out in a staged batch process, in a staged metered monomer addition process, or the polymerization can be initiated as a batch process and then the bulk of the monomers can be continuously staged into the reactor (seed process). In addition, a polymer prepared in accordance with the first stage monomer and crosslinker amounts and a polymer prepared in accordance with the second stage monomer and crosslinker amounts may be prepared separately and subsequently blended. Typically, the polymerization process is carried out at a reaction temperature in the range of about 20 to about 99° C., however, higher or lower temperatures can be used. To facilitate emulsification of the monomer mixture, the emulsion polymerization is carried out in the presence of at least one surfactant. In one embodiment, the emulsion polymerization is carried out in the presence of surfactant ranging in the amount of about 1% to about 10% by weight in one aspect, from about 3% to about 8% in another aspect, and from about 3.5% to about 7% by weight in a further aspect, based on a total emulsion weight basis. The emulsion polymerization reaction mixture also includes one or more free radical initiators which are present in an amount ranging from about 0.01% to about 3% by weight based on total monomer weight. The polymerization can be performed in an aqueous or aqueous alcohol medium.

Surfactants for facilitating emulsion polymerizations include anionic, nonionic, amphoteric, and cationic surfactants, as well as mixtures thereof. Most commonly, anionic and nonionic surfactants can be utilized as well as mixtures thereof.

Suitable anionic surfactants for facilitating emulsion polymerizations are well-known in the art and include, but are not limited to, sodium lauryl sulfate, sodium dodecyl benzene sulfonate, sodium ($C_6$-$C_{16}$) alkyl phenoxy benzene sulfonate, disodium ($C_6$-$C_{16}$) alkyl phenoxy benzene sulfonate, disodium ($C_6$-$C_{16}$) di-alkyl phenoxy benzene sulfonate, disodium laureth-3 sulfosuccinate, sodium dioctyl sulfosuccinate, sodium di-sec-butyl naphthalene sulfonate, disodium dodecyl diphenyl ether sulfonate, disodium n-octadecyl sulfosuccinate, phosphate esters of branched alcohol ethoxylates, and the like.

Nonionic surfactants suitable for facilitating emulsion polymerizations are well-known in the polymer art, and include, without limitation, linear or branched $C_8$-$C_{30}$ fatty alcohol ethoxylates, such as capryl alcohol ethoxylate, lauryl alcohol ethoxylate, myristyl alcohol ethoxylate, cetyl alcohol ethoxylate, stearyl alcohol ethoxylate, cetearyl alcohol ethoxylate, sterol ethoxylate, oleyl alcohol ethoxylate, and, behenyl alcohol ethoxylate; alkylphenol alkoxylates, such as octylphenol ethoxylates; and polyoxyethylene polyoxypropylene block copolymers, and the like. Additional fatty alcohol ethoxylates suitable as non-ionic surfactants are described below. Other useful nonionic surfactants include $C_8$-$C_{22}$ fatty acid esters of polyoxyethylene glycol, ethoxylated mono- and diglycerides, sorbitan esters and ethoxylated sorbitan esters, $C_8$-$C_{22}$ fatty acid glycol esters, block copolymers of ethylene oxide and propylene oxide, and combinations thereof. The number of ethylene oxide units in each of the foregoing ethoxylates can range from 2 and above in one aspect, and from 2 to about 150 in another aspect.

Exemplary free radical initiators include, but are not limited to, water-soluble inorganic persulfate compounds, such as ammonium persulfate, potassium persulfate, and sodium persulfate; peroxides such as hydrogen peroxide, benzoyl peroxide, acetyl peroxide, and lauryl peroxide; organic hydroperoxides, such as cumene hydroperoxide and t-butyl hydroperoxide; organic peracids, such as peracetic acid; and oil soluble, free radical producing agents, such as 2,2'-azobisisobutyronitrile, and the like, and mixtures thereof. Peroxides and peracids can optionally be activated with reducing agents, such as sodium bisulfite, sodium formaldehyde, or ascorbic acid, transition metals, hydrazine, and the like. Particularly suitable free-radical polymerization initiators include water soluble azo polymerization initiators, such as 2,2'-azobis(tert-alkyl) compounds having a water solubilizing substituent on the alkyl group. Preferred azo polymerization catalysts include the Vazo® free-radical polymerization initiators, available from DuPont, such as Vazo® 44 (2,2'-azobis(2-(4,5-dihydroimidazolyl)propane), Vazo® 56 (2,2'-azobis(2-methylpropionamidine) dihydrochloride), and Vazo® 68 (4,4'-azobis(4-cyanovaleric acid)).

Optionally, other emulsion polymerization additives and processing aids which are well-known in the emulsion polymerization art, such as auxiliary emulsifiers, solvents, buffering agents, chelating agents, inorganic electrolytes, polymeric stabilizers, and pH adjusting agents can be included in the polymerization system.

In one aspect, an auxiliary emulsifying aid selected from an ethoxylated $C_{10}$ to $C_{22}$ fatty alcohol (or their mixtures) can be added to the polymerization medium. In one aspect, the fatty alcohol contains from about 1 to about 250 moles of ethoxylation, from about 5 to 100 moles in another aspect, and from about 10 to 50 moles in a further aspect. Exemplary ethoxylated fatty alcohols include lauryl alcohol ethoxylate, myristyl alcohol ethoxylate, cetyl alcohol ethoxylate, stearyl alcohol ethoxylate, cetearyl alcohol ethoxylate, sterol ethoxylate, oleyl alcohol ethoxylate, and behenyl alcohol ethoxylate. In another aspect, suitable ethoxylated fatty alcohols include Ceteth-20, Ceteareth-20, and Steareth-20, Behenth-25, and mixtures thereof.

If employed, the amount of ethoxylated fatty alcohol can range from about 0.1% to 10% by weight in one aspect, from about 0.5% to about 8% by weight in another aspect, and from about 1% to about 5% by weight in a further aspect, based on the total weight percent of the monomers present in the polymerization medium.

In a typical two-stage polymerization, a mixture of the stage monomer mixture is added to a first reactor under inert atmosphere to a solution of emulsifying surfactant (e.g., anionic surfactant) in water. Optional processing aids can be added as desired (e.g., auxiliary emulsifier(s)). The contents of the reactor are agitated to prepare a monomer emulsion. To a second reactor equipped with an agitator, an inert gas inlet, and feed pumps are added under inert atmosphere a desired amount of water and additional anionic surfactant and optional processing aids. The contents of the second reactor are heated with mixing agitation. After the contents of the second reactor reaches a temperature in the range of about 45 to 98° C., a free radical initiator is injected into the so formed aqueous surfactant solution in the second reactor, and a portion of the monomer emulsion from the first reactor is gradually metered into the second reactor over a period typically ranging from about one half to about four hours. The reaction temperature is controlled in the range of about 45 to about 95° C. After completion of the first stage monomer addition, an additional quantity of free radical initiator can optionally be added to the second reactor and the resulting reaction mixture is typically held at a temperature of about 45 to 95° C. for a time period sufficient to complete or substantially complete the polymerization reaction and obtain a latex emulsion containing particles of the first stage polymer segment.

The second stage monomer emulsion prepared from the second stage monomer mixture can be formed in a separate reactor following the same procedures as outlined for formulating the first stage emulsion of monomers. The second stage monomer emulsion is metered or batched into the second reactor at a constant rate and mixed with the first stage polymer emulsion. Simultaneous with the second stage monomer feed, a free radical initiator in an amount sufficient to initiate polymerization is metered into the reaction mixture and the second stage monomers are polymerized in the presence of the first stage polymer segment. The temperature is maintained at about 85° C. for about 2.5 hours or until polymerization is complete. Unreacted monomer can be eliminated by addition of more initiator, as is well-known in the emulsion polymerization art. Typically, the staged polymer emulsion product has a total polymer solids (total active polymer) content ranging from about 10 to about 45 weight percent (based on the weight of the total emulsion). While the polymer is synthesized in an emulsion, it should be recognized that the staged polymer can be supplied in dried powder form if desired.

Cleansing Surfactants

In one aspect, an embodiment of the present technology relates to stable, aqueous cleansing compositions comprising a staged acrylic based polymeric rheology modifier and a surfactant(s). Suitable surfactants include anionic, amphoteric, cationic and nonionic surfactants, as well as mixtures thereof. Such compositions are useful in personal care cleansing compositions that contain various components that require stable suspension, such as, for example, substantially insoluble active materials, benefit agents and aesthetic agents. (e.g., silicones, oily materials, pearlescent and iridescent materials, aesthetic cosmetic glitters, cosmeceutical beads and particles, gaseous bubbles, exfoliants, and the like).

In one aspect of the present technology, suitable anionic surfactants include but are not limited to alkyl sulfates, alkyl ether sulfates, alkyl sulphonates, alkaryl sulfonates, α-olefin-sulphonates, alkylamide sulphonates, alkarylpolyether sulphates, alkylamidoether sulfates, alkyl monoglyceryl ether sulfates, alkyl monoglyceride sulfates, alkyl monoglyceride sulfonates, alkyl succinates, alkyl sulfosuccinates, alkyl ether sulfosuccinates, alkyl sulfosuccinamates, alkyl amidosulfosuccinates; alkyl sulfoacetates, alkyl phosphates, alkyl ether phosphates, alkyl ether carboxylates, alkyl amidoethercarboxylates, acyl lactylates, alkyl isethionates, acyl isethionates, carboxylate salts and amino acid derived surfactants such as N-alkyl amino acids, N-acyl amino acids, as well as alkyl peptides. Mixtures of these anionic surfactants are also useful.

In one aspect, the cation moiety of the forgoing surfactants is selected from sodium, potassium, magnesium, ammonium, and alkanolammonium ions such as monoethanolammonium, diethanolammonium triethanolammonium ions, as well as monoisopropylammonium, diisopropylammonium and triisopropylammonium ions. In one embodiment, the alkyl and acyl groups of the foregoing surfactants contain from about 6 to about 24 carbon atoms in one aspect, from 8 to 22 carbon atoms in another aspect and from about 12 to 18 carbon atoms in a further aspect and may be unsaturated. The aryl groups in the surfactants are selected from phenyl or benzyl. The ether containing surfactants set forth above can contain from 1 to 10 ethylene oxide and/or propylene oxide units per surfactant molecule in one aspect, and from 1 to 3 ethylene oxide units per surfactant molecule in another aspect.

Examples of suitable anionic surfactants include the sodium, potassium, lithium, magnesium, and ammonium salts of laureth sulfate, trideceth sulfate, myreth sulfate, $C_{12}$-$C_{13}$ pareth sulfate, $C_{12}$-$C_{14}$ pareth sulfate, and $C_{12}$-$C_{15}$ pareth sulfate, ethoxylated with 1, 2, and 3 moles of ethylene oxide; the sodium potassium, lithium, magnesium, ammonium, and triethanolammonium salts of lauryl sulfate, coco sulfate, tridecyl sulfate, myristyl sulfate, cetyl sulfate, cetearyl sulfate, stearyl sulfate, oleyl sulfate, and tallow sulfate, disodium lauryl sulfosuccinate, disodium laureth sulfosuccinate, sodium cocoyl isethionate, sodium lauroyl isethionate, sodium lauroyl methyl isethionate, sodium $C_{12}$-$C_{14}$ olefin sulfonate, sodium laureth-6 carboxylate, sodium dodecylbenzene sulfonate, triethanolamine monolauryl phosphate, and fatty acid soaps, including the sodium, potassium, ammonium, and triethanolamine salts of a saturated and unsaturated fatty acids containing from about 8 to about 22 carbon atoms.

In one aspect, the amino acid surfactants are selected from a N-acyl amino acid of the formula:

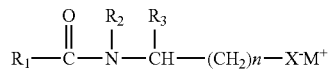

wherein $R_1$ is a saturated or unsaturated, straight or branched alkyl chain containing 7 to 17 carbon atoms, $R_2$ is H or a methyl group, $R_3$ is H, COO$^-$M$^+$, CH$_2$COO$^-$M$^+$ or COOH, n is 0 to 2, X is COO$^-$ or SO$_3^-$ and M independently represents H, sodium, potassium, ammonium or triethanolammonium.

In one aspect, the N-acyl amino acid surfactants represented by the formula immediately above are derived from taurates, glutamates, alanine, alaninates, sacosinates, aspartates, glycinates, and mixtures thereof.

Representative taurate surfactants conform to the formula:

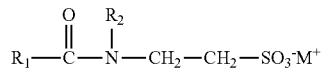

wherein R₁ is a saturated or unsaturated, straight or branched alkyl chain containing 7 to 17 carbon atoms in one aspect and 9 to 13 carbon atoms in another aspect, $R_2$ is H or methyl, and M is H, sodium, potassium, ammonium or triethanolammonium.

Non-limiting examples of taurate surfactants are potassium cocoyl taurate, potassium methyl cocoyl taurate, sodium caproyl methyl taurate, sodium cocoyl taurate, sodium lauroyl taurate, sodium methyl cocoyl taurate, sodium methyl lauroyl taurate, sodium methyl myristoyl taurate, sodium methyl oleoyl taurate, sodium methyl palmitoyl taurate, sodium methyl stearoyl taurate, and mixtures thereof.

Representative glutamate surfactants conform to the formula:

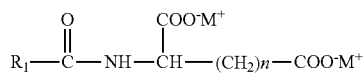

wherein $R_1$ is a saturated or unsaturated, straight or branched alkyl chain containing 7 to 17 carbon atoms in one aspect and 9 to 13 carbon atoms in another aspect, n is 0 to 2, and M independently is H, sodium, potassium, ammonium or triethanolammonium.

Non-limiting examples of glutamate surfactants are di-potassium capryloyl glutamate, di-potassium undecylenoyl glutamate, di-sodium capryloyl glutamate, di-sodium cocoyl glutamate, di-sodium lauroyl glutamate, di-sodium stearoyl glutamate, di-sodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, and mixtures thereof.

Representative alanine and alaninate surfactants conform to the formula:

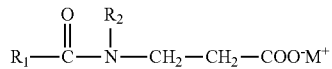

wherein $R_1$ is a saturated or unsaturated, straight or branched alkyl chain containing 7 to 17 carbon atoms in one aspect and 9 to 13 carbon atoms in another aspect, $R_2$ is H or methyl, and M is H, sodium, potassium, ammonium or triethanolammonium.

Non-limiting examples of alanine and alaninate surfactants are cocoyl methyl β-alanine, lauroyl β-alanine, lauroyl methyl β-alanine, myristoyl β-alanine, potassium lauroyl methyl β-alanine, sodium cocoyl alaninate, sodium cocoyl methyl β-alanine, sodium myristoyl methyl β-alanine, and mixtures thereof.

Representative glycinate surfactants conform to the formula:

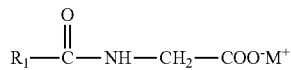

wherein $R_1$ is a saturated or unsaturated, straight or branched alkyl chain containing 7 to 17 carbon atoms in one aspect and 9 to 13 carbon atoms in another aspect, and M is H, sodium, potassium, ammonium or triethanolammonium.

Non-limiting examples of glycinate surfactants are sodium palmitoyl glycinate, sodium lauroyl glycinate, sodium cocoyl glycinate, sodium myristoyl glycinate, potassium lauroyl glycinate, potassium cocoyl glycinate, sodium stearoyl glycinate, and mixtures thereof.

Representative sarcosinate surfactants conform to the formula:

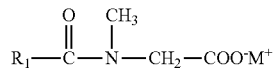

wherein $R_1$ is a saturated or unsaturated, straight or branched alkyl chain containing 7 to 17 carbon atoms in one aspect and 9 to 13 carbon atoms in another aspect, and M is H, sodium, potassium, ammonium or triethanolamine.

Non-limiting examples of sarcosinate surfactants are potassium lauroyl sarcosinate, potassium cocoyl sarcosinate, sodium cocoyl sarcosinate, sodium lauroyl sarcosinate, sodium myristoyl sarcosinate, sodium palmitoyl sarcosinate, and mixtures thereof.

Representative aspartate surfactants conform to the formula:

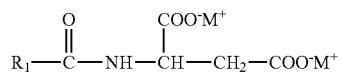

wherein $R_1$ is a saturated or unsaturated, straight or branched alkyl chain containing 7 to 17 carbon atoms in one aspect and 9 to 13 carbon atoms in another aspect, and M independently is H, sodium, potassium, ammonium or triethanolammonium.

Non-limiting examples of aspartate surfactants are sodium lauroyl aspartate, sodium myristoyl aspartate, sodium cocoyl aspartate, sodium caproyl aspartate, di-sodium lauroyl aspartate, di-sodium myristoyl aspartate, di-sodium cocoyl aspartate, di-sodium caproyl aspartate, potassium lauroyl aspartate, potassium myristoyl aspartate, potassium cocoyl aspartate, potassium caproyl aspartate, di-potassium lauroyl aspartate, di-potassium myristoyl aspartate, di-potassium cocoyl aspartate, di-potassium caproyl aspartate, and mixtures thereof.

In one aspect of the present technology, suitable amphoteric surfactants include but are not limited to alkyl betaines, e.g., lauryl betaine; alkylamido betaines, e.g., cocamidopropyl betaine and cocohexadecyl dimethylbetaine; alkylamido sultaines, e.g., cocamidopropyl hydroxysultaine; (mono- and di-) amphocarboxylates, e.g., sodium cocoamphoacetate, sodium lauroamphoacetate, sodium capryloamphoacetate, disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, and disodium capryloamphodipropionate; and mixtures thereof.

The foregoing amphoteric surfactants (i.e., the betaines and sultaines are disclosed without a counter ion, as one of ordinary skill in the art will recognize that the under the pH conditions of the compositions containing the amphoteric surfactants, these surfactants are either electrically neutral by virtue of having balancing positive and negative charges, or they contain counter ions such as alkali metal, alkaline earth or ammonium ions as a charge balancing moiety.

In one aspect of the present technology, suitable cationic surfactants include but are not limited to alkylamines, amidoamines, alkyl imidazolines, ethoxylated amines, quaternary compounds, and quaternized esters. In addition, alkylamine oxides can function as a cationic surfactant at a lower pH values.

Non-limiting examples of alkylamines and salts thereof include dimethyl cocamine, dimethyl palmitamine, dioctylamine, dimethyl stearamine, dimethyl soyamine, soyamine, myristyl amine, tridecyl amine, ethyl stearylamine, N-tallowpropane diamine, ethoxylated stearylamine, dihydroxy ethyl stearylamine, arachidylbehenylamine, dimethyl lauramine, stearylamine hydrochloride, soyamine chloride, stearylamine formate, N-tallowpropane diamine dichloride, and amodimethicone (INCI name for a silicone polymer and blocked with amino functional groups, such as aminoethylamino propylsiloxane).

Non-limiting examples of amidoamines and salts thereof include stearamido propyl dimethyl amine, stearamidopropyl dimethylamine citrate, palmitamidopropyl diethylamine, and cocamidopropyl dimethylamine lactate.

Non-limiting examples of alkyl imidazoline surfactants include alkyl hydroxyethyl imidazoline, such as stearyl hydroxyethyl imidazoline, coco hydroxyethyl imidazoline, ethyl hydroxymethyl oleyl oxazoline, and the like.

Non-limiting examples of ethyoxylated amines include PEG-cocopolyamine, PEG-15 tallow amine, quaternium-52, and the like.

Exemplary quaternary ammonium surfactants include, but are not limited to cetyl trimethylammonium chloride, cetylpyridinium chloride, dicetyl dimethyl ammonium chloride, dihexadecyl dimethyl ammonium chloride, stearyl dimethyl benzyl ammonium chloride, dioctadecyl dimethyl ammonium chloride, dieicosyl dimethyl ammonium chloride, didocosyl dimethyl ammonium chloride, dihexadecyl dimethyl ammonium chloride, dihexadecyl dimethyl ammonium acetate, behenyl trimethyl ammonium chloride, benzalkonium chloride, benzethonium chloride, and di(cocoalkyl) dimethyl ammonium chloride, ditallowdimethyl ammonium chloride, di(hydrogenated tallow) dimethyl ammonium chloride, di(hydrogenated tallow) dimethyl ammonium acetate, ditallowdimethyl ammonium methyl sulfate, ditallow dipropyl ammonium phosphate, and ditallow dimethyl ammonium nitrate.

At low pH values, alkylamine oxides can protonate and behave similarly to N-alkyl amines. Examples include, but are not limited to, dimethyl-dodecylamine oxide, oleyldi(2-hydroxyethyl) amine oxide, dimethyltetradecylamine oxide, di(2-hydroxyethyl)-tetradecylamine oxide, dimethylhexadecylamine oxide, behenamine oxide, cocamine oxide, decyltetradecylamine oxide, dihydroxyethyl $C_{12-15}$ alkoxypropylamine oxide, dihydroxyethyl cocamine oxide, dihydroxyethyl lauramine oxide, dihydroxyethyl stearamine oxide, dihydroxyethyl tallowamine oxide, hydrogenated palm kernel amine oxide, hydrogenated tallowamine oxide, hydroxyethyl hydroxypropyl $C_{12}$-$C_{15}$ alkoxypropylamine oxide, lauramine oxide, myristamine oxide, cetylamine oxide, oleamidopropylamine oxide, oleamine oxide, palmitamine oxide, PEG-3 lauramine oxide, dimethyl lauramine oxide, potassium trisphosphonomethylamine oxide, soyamidopropylamine oxide, cocamidopropylamine oxide, stearamine oxide, tallowamine oxide, and mixtures thereof.

The nonionic surfactant can be any of the nonionic surfactants known or previously used in the art of aqueous surfactant compositions. Suitable nonionic surfactants include but are not limited to aliphatic $C_6$ to $C_{18}$ primary or secondary linear or branched chain acids, alcohols or phenols, linear alcohol and alkyl phenol alkoxylates (especially ethoxylates and mixed ethoxy/propoxy), block alkylene oxide condensate of alkyl phenols, alkylene oxide condensates of alkanols, ethylene oxide/propylene oxide block copolymers, semi-polar nonionics (e.g., amine oxides and phosphine oxides), as well as alkyl amine oxides. Other suitable nonionics include mono or di alkyl alkanolamides and alkyl polysaccharides, sorbitan fatty acid esters, polyoxyethylene sorbitan fatty acid esters, polyoxyethylene sorbitol esters, and polyoxyethylene acids. Examples of suitable nonionic surfactants include coco mono- or diethanolamide, cocamidopropyl and lauramine oxide, polysorbate 20, 40, 60 and 80, ethoxylated linear alcohols, cetearyl alcohol, lanolin alcohol, stearic acid, glyceryl stearate, PEG-150 distearate, PEG-100 stearate, PEG-80 sorbitan laurate, and oleth 20. Other suitable nonionic surfactants include the alkyl glucosides and the alkyl polyglucosides, such as, for example, coco-glucoside, decyl glucoside, lauryl glucoside, decyl diglucoside, lauryl diglucoside and coco diglucoside.

In one aspect, the nonionic surfactant is an alcohol alkoxylate derived from a saturated or unsaturated fatty alcohol containing 8 to 18 carbon atoms, and the number of alkylene oxide groups present in the alcohol range from about 3 to about 12. The alkylene oxide moiety is selected from ethylene oxide, propylene oxide and combinations thereof. In another aspect, the alcohol alkoxylate is derived from a fatty alcohol containing 8 to 15 carbon atoms and contains from 5 to 10 alkoxy groups (e.g. ethylene oxide, propylene oxide, and combinations thereof). Exemplary nonionic fatty alcohol alkoxylate surfactants in which the alcohol residue contains 12 to 15 carbon atoms and contain about 7 ethylene oxide groups are available under the Tomadol® (e.g., product designation 25-7) and Neodol® (e.g., product designation 25-7) trade names from Tomah Products, Inc. and Shell Chemicals, respectively.

An exemplary nonionic alcohol alkoxylated surfactant derived from an unsaturated fatty alcohol and containing about 10 ethylene oxide groups is available from Lubrizol Advanced Materials, Inc. under the trade Chemonic™ oleth-10 ethoxylated alcohol.

Another commercially available alcohol alkoxylate surfactant is sold under the Plurafac® trade name from BASF. The Plurafac surfactants are reaction products of a higher linear alcohol and a mixture of ethylene and propylene oxides, containing a mixed chain of ethylene oxide and propylene oxide, terminated by a hydroxyl group. Examples include $C_{13}$ to $C_{15}$ fatty alcohols condensed with 6 moles ethylene oxide and 3 moles propylene oxide, $C_{13}$ to $C_{15}$ fatty alcohols condensed with 7 moles propylene oxide and 4 moles ethylene oxide, and $C_{13}$ to $C_{15}$ fatty alcohols condensed with 5 moles propylene oxide and 10 moles ethylene oxide.

Another commercially suitable nonionic surfactant is available from Shell Chemicals under the Dobanol™ trade name (product designations 91-5 and 25-7). Product designation 91-5 is an ethoxylated $C_9$ to $C_{11}$ fatty alcohol with an average of 5 moles ethylene oxide and product designation 25-7 is an ethoxylated $C_{12}$ to $C_{15}$ fatty alcohol with an average of 7 moles ethylene oxide per mole of fatty alcohol.

Another commercially suitable nonionic surfactant is available from Shell Chemicals under the Dobanol™ trade name (product designations 91-5 and 25-7). Product designation 91-5 is an ethoxylated $C_9$ to $C_{11}$ fatty alcohol with an average of 5 moles ethylene oxide and product designation 25-7 is an ethoxylated $C_{12}$ to $C_{15}$ fatty alcohol with an average of 7 moles ethylene oxide per mole of fatty alcohol.

Other surfactants which can be utilized in the cleansing compositions of the present technology are set forth in more detail in WO 99/21530, U.S. Pat. Nos. 3,929,678, 4,565,647, 5,456,849, 5,720,964, 5,858,948, and 7,115,550, which are herein incorporated by reference. Additionally, suitable surfactants are described in McCutcheon's Emulsifiers and Detergents (North American and International Editions, by Schwartz, Perry and Berch) which is hereby fully incorporated by reference.

In one aspect, the surfactant(s) utilized in the surfactant containing composition can be employed in amounts typically utilized in personal care cleansing compositions. In another aspect, the amount of surfactant(s) can range from about 0.1 wt. % to about 50 wt. %, in a further aspect, the amount of surfactant(s) ranges from about 0.5 wt. % to about 45 wt. %, from about 1 wt. % to about 30 wt. % in a still further aspect, from about 1.5 wt. % to about 25 wt. %, and from about 3 wt. % to about 15 wt. %, and from about 5 wt. % to about 10 wt. % (all percentages based on the weight of the total composition).

In one aspect, the surfactant is selected from a combination of an anionic surfactant and an amphoteric surfactant. In one aspect, the ratio of anionic surfactant to amphoteric surfactant (active material) is 10:1 to about 2:1 in one aspect, and 9:1, 8:1, 7:1 6:1, 5:1, 4.5:1, 4:1, or 3:1 in another aspect.

Water is utilized as a diluent in the cleansing compositions of the present technology. In one aspect, the amount of water can range from about 5 wt. % to about 95 wt. % of the weight of the total surfactant containing composition. In another aspect the amount of water can range from about 10 wt. % to about 90 wt. %, from about 20 wt. % to about 80 wt. % in a further aspect, and from about 30 wt. % to about 75 wt. % in a still further aspect, based on the total weight of the surfactant containing composition.

In one aspect, the staged acrylic emulsion copolymers of the disclosed technology are free of any monomeric repeating unit residues other than the repeating unit residues polymerized from at least one ethylenically unsaturated $C_3$-$C_6$ carboxylic acid monomer and at least one $C_1$-$C_4$ alkyl (meth)acrylate monomer and a crosslinking monomer. When an optional chain transfer agent is utilized to prepare the polymers of the disclosed technology, the polymers will contain a residue of the chain transfer agent.

In one aspect, the staged acrylic emulsion copolymer of the disclosed technology has an acid number 300 (calculated on the basis of mEq. of KOH/g of polymer). In one aspect, the acid number ranges from 310 to about 450, from about 315 to about 400, and from about 320 to about 350.

In one aspect, the staged acrylic emulsion polymers of the disclosed technology have a viscosity of 5,000-20,000 mPa·s or less (Brookfield RV, 20 rpm, spindle No. 4 or No. 5) at a 2.5 wt. % polymer solids concentration in deionized water and neutralized to a pH of about 6.8 to about 7.3 with a 20 wt. % NaOH solution. In another aspect, the mucilage viscosity ranges from about 7,000 to about 18,000 mPa·s, from about 8,000 to about 15,000 mPa·s in a further aspect, and from about 9,000 to about 14,000 mPa·s in a still further aspect.

In one aspect, the staged acrylic emulsion polymers of the disclosed technology at a 2.5 wt. % polymer solids concentration in deionized water and neutralized to a pH of about 6.8 to about 7.3 with a 20 wt. % NaOH solution has a clarity value (turbidity) of less than 52 NTU in one aspect, less than 45 NTU in another aspect, less than 35 NTU in a further aspect, and less than 25 NTU in a still further aspect.

In one aspect, a neat emulsion containing about 25 wt. % solids of the staged acrylic polymers of the disclosed technology has a minimum film formation temperature (MFFT) ranging from about 18° to about 45° C. in one aspect, from about 20° to about 35° C. in another aspect, from about 22° to about 30° C. in a further aspect, and from about 23° to about 28° C. in a still further aspect.

The staged acrylic emulsion copolymers can be utilized in surfactant compositions in the un-neutralized state or can be neutralized to a desired degree of neutralization with a suitable alkaline neutralizing agent. The amount of alkaline neutralizing agent employed to obtain a desired degree of neutralization is calculated on the basis of the acid number of the polymer. Exemplary neutralizing agents include sodium hydroxide, potassium hydroxide, triethanolamine, fatty acid amines, and the like. Alternatively, other alkaline materials can be used, such as, for example, pre-neutralized surfactants. In one aspect, the degree of polymer neutralization is 100% or less, in another aspect the degree of polymer neutralization is 80% or less, in still another aspect the degree of polymer neutralization is 60% or less. In a further aspect, the degree of neutralization is 50% or less.

In one aspect, the staged acrylic copolymer of the disclosed technology may be added to a composition comprising at least one detersive surfactant. The surfactant composition can be neutralized with an alkaline neutralization agent (described above) to achieve a final pH value ranging from about 4 to about 8 in one aspect, from about 4.5 to about 7.5 in another aspect and from about 5 to about 7 in a further aspect. The alkaline neutralization agent can be added to the surfactant composition at any stage in the formulation process, if the desired final pH of the formulation is attained, and the desired formulation properties are not deleteriously impacted.

The amount of staged acrylic emulsion copolymer utilized in surfactant containing compositions of the disclosed technology, such as, for example, personal care cleansing, animal and pet care cleansing, household care cleaning, and industrial and institutional cleaning compositions can range from about 0.05 wt. % to about 10 wt. % (active polymer solids) in one aspect, from about 0.1 wt. % to 6 wt. %, from about 0.5 wt. % to 4 wt. %, and from about 1 wt. % to about 3 wt. % in further aspects, and from about 1.25 wt. % to about 2.5 wt. % based on the total weight of the composition.

The surfactant compositions of the present technology can contain one or more of a wide variety of components well-known to those skilled in the art, such as botanicals, chelators, humectant skin or hair conditioners, lubricants, moisture barriers/emollients, opacifiers, preservatives, spreading aids, conditioning polymers, vitamins, viscosity adjusters, viscosity modifiers (auxiliary thickeners), emulsifiers, perfumes, fragrances, fragrance oils, suspended beads, enzymes, builders, electrolytes (e.g., NaCl), buffers, hydrotropes (e.g., ethanol, sodium xylene sulfonate, and sodium cumene sulfonate), inorganics (e.g., clay, bentonite, kaolin), particulate materials, soil releasing agents, color additives, as well as the numerous other optional components for enhancing and maintaining the properties and aesthetics of the personal care compositions. Such components are also described in detail in well-known sources such as Mitchell C. Schlossman, The Chemistry and Manufacture of Cosmetics, Volumes I and II, Allured Publishing Corporation, 2000.

Botanical materials can include any water soluble or oil soluble material extracted from a particular plant, fruit, nut, or seed. Suitable botanicals can include, for example, Aloe barbadensis leaf juice, *Echinacea* (e.g., sp. *angustifolia, purpurea, pallida*), yucca glauca, willow herb, basil leaves, Turkish oregano, carrot root, grapefruit, fennel seed, rosemary, tumeric, thyme, blueberry, bell pepper, blackberry, spirulina, black currant fruit, tea leaves, such as for, example, Chinese tea, black tea (e.g., var. Flowery Orange Pekoe, Golden Flowery Orange Pekoe, Fine Tippy Golden Flowery Orange Pekoe), green tea (e.g., var. Japanese, Green Darjeeling), oolong tea, coffee seed, dandelion root, date palm fruit, gingko leaf, green tea, hawthorn berry, licorice, sage, strawberry, sweet pea, tomato, vanilla fruit, comfrey, arnica, centella asiatica, cornflower, horse chestnut, ivy, magnolia, oat, pansy, skullcap, seabuckthorn, white nettle, and witch hazel. Botanicals include, for example, chlorogenic acid, glutathione, glycrrhizin, neohesperidin, quercetin, rutin, morin, myricetin, absinthe, and chamomile.

Botanicals can be present in an amount ranging from about 0.001% to about 10% by weight, from about 0.005% to about 8% by weight in another aspect, and from about 0.01% to about 5% by weight in a further aspect, based of the total weight of the composition.

Suitable chelators include EDTA (ethylene diamine tetraacetic acid) and salts thereof such as disodium EDTA and tetrasodium ETDA, citric acid and salts thereof, tetrasodium glutamate diacetate, cyclodextrins, and the like, and mixtures thereof. Such suitable chelators typically comprise from about 0.001 wt. % to about 3 wt. % in one aspect, from about 0.01 wt. % to about 2 wt. % in another aspect, and from about 0.01 wt. % to about 1 wt. % in a further aspect of the present technology based on the total weight of the surfactant containing composition.

Suitable humectants include allantoin; pyrrolidonecarboxylic acid and its salts; hyaluronic acid and its salts; sorbic acid and its salts, salicylic acid and its salts; urea, hydroxyethyl urea; lysine, arginine, cystine, guanidine, and other amino acids; polyhydroxy alcohols such as glycerin, propylene glycol, hexylene glycol, hexanetriol, ethoxydiglycol, dimethicone copolyol, and sorbitol, and the esters thereof; polyethylene glycol; glycolic acid and glycolate salts (e.g. ammonium and quaternary alkyl ammonium); lactic acid and lactate salts (e.g. ammonium and quaternary alkyl ammonium); sugars and starches; sugar and starch derivatives (e.g. alkoxylated methyl glucose ethers, such as PPG-20 methyl glucose ether); D-panthenol; lactamide monoethanolamine; acetamide monoethanolamine; and the like, and mixtures thereof. Preferred humectants include the $C_3$ to $C_6$ diols and triols, such as glycerin, propylene glycol, 1,3-propanediol, hexylene glycol, hexanetriol, and the like, and mixtures thereof. Such suitable humectants typically comprise from about 1 wt. % to about 10 wt. % in one aspect, from about 2 wt. % to about 8 wt. % in another aspect, and from about 3 wt. % to about 5 wt. % in a further aspect of the present technology, based on the total weight of the surfactant containing composition.

Suitable moisture barriers and or emollients include mineral oil; stearic acid; fatty alcohols such as cetyl alcohol, cetearyl alcohol, myristyl alcohol, behenyl alcohol, and lauryl alcohol; cetyl acetate in acetylated lanolin alcohol, isostearyl benzoate, dicaprylyl maleate, caprylic and capric triglyceride; petrolatum, lanolin, coco butter, *Avena sativa* (oat) kernel oil, shea butter, beeswax and esters there of; ethoxylated fatty alcohol esters such as ceteareth-20, oleth-5, and ceteth-5; avocado oil or glycerides; sesame oil or glycerides; safflower oil or glycerides; sunflower oil or glycerides; botanical seed oils; volatile silicone oils; non-volatile emollients, and the like, and mixtures thereof.

Suitable non-volatile emollients include fatty acid and fatty alcohol esters, highly branched hydrocarbons, and the like, and mixtures thereof. Such fatty acid and fatty alcohol esters include decyl oleate, butyl stearate, myristyl myristate, octyldodecyl stearoylstearate, octylhydroxystearate, di-isopropyl adipate, isopropyl myristate, isopropyl palmitate, ethyl hexyl palmitate, isodecyl neopentanoate $C_{12}$ to $C_{15}$ alcohol benzoate, diethyl hexyl maleate, PPG-14 butyl ether and PPG-2 myristyl ether propionate, cetearyl octanoate, and the like, and mixtures thereof. Suitable highly branched hydrocarbons include isohexadecane and the like, and mixtures thereof. Such suitable moisture barriers and/or emollients, alone or in combination, typically comprise from about 1 wt. % to about 20 wt. % in one aspect, from about 2 wt. % to about 15 wt. % in another aspect, and from about 3 wt. % to about 10 wt. % in a further aspect of the present technology, based on the total weight of the surfactant containing composition.

Suitable opacifiers include glycol fatty acid esters; alkoxylated fatty acid esters; polymeric opacifiers, fatty acid alcohols; hydrogenated fatty acids, waxes and oils; kaolin; magnesium silicate; titanium dioxide; silica; and the like, and mixtures thereof. Such suitable opacifiers typically comprise from about 0.01 wt. % to about 8 wt. % in one aspect, from about 0.05 wt. % to about 6 wt. % in another aspect, and from about 0.1 wt. % to about 5 wt. % in a further aspect of the present technology, based on the total weight of the surfactant containing composition.

Suitable preservatives include compounds that have antifungal activity, antimicrobial activity, antioxidant activity, UV protection activity, and the like. polymethoxy bicyclic oxazolidine, methylparaben, propylparaben, ethylparaben, butylparaben, benzyltriazole, DMDM hydantoin (also known as 1,3-dimethyl-5,5-dimethyl hydantoin), imidazolidinyl urea, phenoxyethanol, phenoxyethylparaben, methylisothiazolinone, methylchloroisothiazolinone, benzophenone-4, dibutylhydroxytoluene (BHT), benzoisothiazolinone, triclosan, quaternium-15, salicylic acid salts, and the like, and mixtures thereof.

In lieu of or in combination with the preservatives mentioned immediately above, food grade preservatives can be utilized in the compositions of the disclosed technology. In one aspect, the food grade preservative is selected from one or more organic acids and salts thereof. In one aspect, the organic acid preservative is a carboxylic acid compound represented by the formula: $R^5C(O)OH$, wherein $R^5$ represents hydrogen, a saturated and unsaturated hydrocarbyl group containing 1 to 8 carbon atoms or $C_6$ to $C_{10}$ aryl. In another aspect, $R^5$ is selected from a hydrogen, a $C_1$ to $C_8$ alkyl group, a $C_2$ to $C_8$ alkenyl group, or phenyl. Exemplary acids are, but are not limited to, formic acid, acetic acid, propionic acid, sorbic acid, caprylic acid, oxalic acid, succinic acid, glutaric acid, adipic acid, azelaic acid, maleic acid, fumaric acid, lactic acid, glyceric acid, tartronic acid malic acid, tartaric acid, gluconic acid, citric acid, ascorbic acid, salicylic acid, phthalic acid, mandelic acid, benzilic acid, and benzoic acid, salts thereof, and mixtures thereof.

Salts of the foregoing acids are useful as long as they retain efficacy at low pH values. Suitable salts include the alkali metal (e.g., sodium, potassium, calcium) and ammonium salts of the acids enumerated above.

The preservatives typically comprise about 0.01 wt. % to about 1.5 wt. % in one aspect, from about 0.1 wt. % to about 1 wt. % in another aspect, and from about 0.3 wt. % to about 1 wt. % in a further aspect, based on the total weight of the composition.

Suitable spreading aids include hydroxypropyl methylcellulose, hydrophobically modified cellulosics, xanthan gum, cassia gum, guar gum, locust bean gum, dimethicone copolyols of various degrees of alkoxylation, boron nitride, talc, and the like, and mixtures thereof. Such suitable spreading aids typically comprise about 0.01 wt. % to about 5 wt. % in one aspect, from about 0.1 wt. % to about 3 wt. % in another aspect, and from about 0.1 wt. % to about 2.0 wt. % in a further aspect, based on the total weight of the surfactant containing composition.

Suitable conditioning polymers include quaternized polygalactomannans such as cationic guar (e.g., guar hydroxypropyltrimonium chloride), cationic cassia (e.g., cassia hydroxypropyltrimonium chloride), cationic locust bean, quaternized cellulosics, polyquaternium-4, polyquaternium-5 polyquaternium-6, polyquaternium-7, polyquaternium-10, polyquaternium-11, polyquaternium-22, polyquaternium-39, polyquaternium-44, polyquaternium-47, polyquaternium-53, and the like, and mixtures thereof. Such conditioning agents typically comprise about 0.01 wt. % to about 3 wt. % in one aspect, from about 0.1 wt. % to about 2 wt. % in another aspect, and from about 0.1 wt. % to about 1 wt. % in a further, based on total weight of the surfactant containing composition.

Suitable vitamins include vitamin A, vitamin B, biotin, pantothenic acid, vitamin C, vitamin D, vitamin E, tocopherol acetate, retinyl palmitate, magnesium ascorbyl phosphate, and the like, and derivatives and mixtures thereof.

Suitable viscosity adjusters include isopropyl alcohol, ethanol, benzyl alcohol, sorbitol, propylene glycol, diethylene glycol, triethylene glycol, dimethyl ether, butylene glycol, and the like, and mixtures thereof. Such suitable viscosity adjusters typically comprise from about 0.1 wt. % to about 60 wt. % in one aspect, from about 1 wt. % to about 40 wt. % in another aspect, and from about 5 wt. % to about 20 wt. % in a further aspect based on the total weight of the surfactant containing compositions.

Suitable hydrotropes include sodium xylene sulfonate, sodium toluene sulfonate, sodium styrene sulfonate, sodium cumene sulfonate), and sodium diisopropyl naphthalene. Nonionic hydrotropes such as glycerin, propylene glycol, ethanol and urea can also be employed. The amount of hydrotrope can range from about 0.05 to about 10 wt. % in one aspect, from about 0.1 to about 5 wt. % in another aspect, from about 0.2 to about 4 wt. % in still another aspect, and from about 0.5 to about 3 wt. % in a further aspect, based on the weight of the total composition Suitable viscosity modifiers (auxiliary thickeners) include natural, semi-synthetic, and synthetic polymers. Examples of natural and modified natural polymers include xanthan gums, cellulosics, modified cellulosics, starches, polysaccharides, and the like. Examples of synthetic polymers include crosslinked polyacrylates, alkali swellable emulsion acrylate copolymers, hydrophobically modified alkali swellable copolymers, hydrophobically modified non-ionic polyurethanes, hydrophobically modified alkoxylated methyl glucosides, such as PEG-120 methyl glucose dioleate, PEG-120 methyl glucose trioleate, and the like. Mixtures can also be used. Such suitable viscosity modifiers/emulsifiers, alone or in combination, typically comprise from about 0.1 wt. % to about 5 wt. % in one aspect, from about 0.3 wt. % to about 3 wt. % in another aspect, and from about 0.5 wt. % to about 2 wt. % in still another aspect, based on the total weight of the surfactant containing compositions.

When used in conjunction with a suspending agent, the surfactant containing composition can contain from about 0.1 wt. % to about 10 wt. %, based on the total weight of the composition of a cosmetic bead component suspended in the composition. Cosmetic beads can be included for aesthetic appearance or can function as micro- and macroencapsulants in the delivery of beneficial agents to the skin. Exemplary bead components include but are not limited to microsponges, gelatin beads; alginate beads; expanded polystyrene beads; jojoba beads; polyethylene beads; Unispheres® cosmetic beads (Induchem), such as for example, product designations YE-501 and UEA-509; Lipopearls™ vitamin E encapsulated in gelatin beads (Lipo Technologies Inc.); and Confetti™ (United Guardian Company). A suitable suspending agent includes a crosslinked acrylic copolymer rheology modifier such as Carbopol® Aqua SF-1 and Carbopol® Aqua SF-2. Such rheology modifiers can be employed in a range of from about 0.1 wt. % to about 5 wt. % (polymer solids), based on the weight of the surfactant containing composition.

Substantially insoluble compounds or materials and particulate materials which require stabilization and/or suspension in the cleansing compositions of the present technology can be utilized. When these materials are utilized in conjunction with formulations that are dispensed from pump containers, such as, for example, a pumpable hand cleanser, the particle size of the particulate material must be of a dimension that passes through the pump mechanism without clogging or fouling the pump after multiple pump cycles. None limiting examples of insoluble compounds and materials that require stable suspension include pigments, exfoliants, anti-dandruff agents and materials used to give a product an aesthetic visual and/or sensory appeal (e.g., mica, polypropylene beads, cosmetic glitters, ethylene glycol, air bubbles, encapsulated fragrances, etc.).

The amount of the particulate component that can be present in the composition ranges from about 0.01% to about 5% by wt. in one aspect, from about 0.05 to about 3 wt. % in another aspect, and from about 0.1% to about 1% by wt. in a further aspect, based on the total weight of the composition.

Other optional components can be used in order to maintain and enhance the properties of personal care compositions. Such optional components include various solvents, propellants, combing aids, pearlizing agents, botanical extracts, antioxidants, antistatic agents, anticorrosion agents, agents suitable for product aesthetics, such as fragrances, perfumes, pigments, dyes, and colorings, and the like.

It is to be recognized that the choice and the amount of ingredients in surfactant containing compositions including the staged acrylic polymers of the present technology will vary depending on the intended product and its function, as is well-known to those skilled in the formulation arts. An extensive listing of substances and their conventional functions and product categories appears in the INCI Dictionary, generally, and in Vol. 2, Sections 4 and 5 of the Seventh Edition, in particular, incorporated herein by reference.

The following examples further describe and demonstrate embodiments within the scope of the present technology. These examples are presented solely for the purpose of illustration and are not to be construed as limitations of the present technology since many variations thereof are possible without departing from the spirit and scope thereof. Unless otherwise specified weight percent (wt. %) is given in weight percent, based on the weight of the total composition.

Methods and Materials

Clarity Testing

The clarity (turbidity) of a composition is determined in Nephelometric Turbidity Units (NTU) employing a nephelometric turbidity meter (Mircro 100 Turbidimeter, HF Scientific, Inc.) at ambient room temperature of about 20 to 25° C. Distilled water (NTU=0) is utilized as a standard. Six-dram screw cap vials (70 mm×25 mm) are filled almost to the top with test sample and centrifuged at 100 rpm until all bubbles are removed. Upon centrifugation, each sample vial is wiped with tissue paper to remove any smudges before placement in the turbidity meter. The sample is placed in the turbidity meter and a reading is taken. Once the reading stabilizes the NTU value is recorded. The vial is given one-quarter turn and another reading is taken and recorded. This is repeated until four readings are taken. The lowest of the four readings is reported as the turbidity value. Lower turbidity values indicate clearer (less turbid) compositions.

Brookfield Viscosity (Mucilage Viscosity)

Viscosity measurements are conducted by the Brookfield method employing a rotating spindle Brookfield viscometer, Model DV2TRV, (Ametek Brookfield), at 20 revolutions per minute (rpm). The polymer mucilage is allowed to equilibrate to a temperature of 25° C. by placing the polymer sample in a water bath for 1 hour before the viscosity measurement is taken. After the equilibration, viscosity is measured at ambient room temperature of about 20 to 25° C. (BV viscosity). Spindle sizes are selected in accordance with the standard operating recommendations from the manufacturer. The artisan of ordinary skill in the art will select a spindle size appropriate for the system to be measured.

Brookfield Viscosity (Surfactant Formulations)

Viscosity measurements for surfactant containing systems are conducted by the Brookfield method employing a rotating spindle Brookfield viscometer, Model DV2TLV Extra, (Ametek Brookfield), at 20 revolutions per minute (rpm), at ambient room temperature of about 20 to 25° C. (BV viscosity). Spindle sizes are selected in accordance with the standard operating recommendations from the manufacturer. The artisan of ordinary skill in the art will select a spindle size appropriate for the system to be measured.

Yield Value

Yield Value, also referred to as Yield Stress, is defined as the initial resistance to flow under stress. It is measured by the Brookfield Yield Value (BYV) Extrapolation Method using a Brookfield viscometer (Model DV2TLV Extra) at ambient room temperature of about 21 to 23° C. The viscometer is used to measure the torque necessary to rotate a spindle through a liquid sample at speeds of 0.5 to 100 rpm. Multiplying the torque reading by the appropriate constant for the spindle and speed gives the apparent viscosity. Yield Value is an extrapolation of measured values to a shear rate of zero. The BYV is calculated by the following equation:

$$BYV, dyn/cm^2 = (\eta_{\alpha 1} - \eta_{\alpha 2})/100$$

where $\eta_{\alpha 1}$ and $\eta_{\alpha 2}$=apparent viscosities obtained at two different spindle speeds (0.5 rpm and 1.0 rpm, respectively). These techniques and the usefulness of the yield value measurement are explained in Technical Data Sheet Number 244 (Revision: 1/2002) from Lubrizol Advanced Materials, Inc., herein incorporated by reference.

Glitter Suspension Test

The ability of a polymer system to suspend active and/or aesthetically pleasing insoluble oily and particulate materials is important from the standpoint of product efficacy and visual appeal. A six-dram vial (approximately 70 mm high× 25 mm in diameter) is filled with 20 g of the formulation to be tested. Each of the sample vials is centrifuged at 1000 rpm for approximately 3 minutes to remove any trapped air bubbles contained in the formulation. Approximately 0.012 g of cosmetic glitter (Starmist Marilyn Red 0023, American Glitters Inc.) having a hexagonal morphology of 0.006 inch, a particle size of 150μ and a density of 1.39-1.42 kg/dm³, is placed on the surface of the sample and gently hand stirred with a wooden spatula until the glitter is uniformly dispersed throughout the sample. The initial position of the glitter particles is noted and marked. After allowing the sample to equilibrate for 2 hours, the sample is then placed in a heated oven and aged for 24 hours at 45° C. After aging at elevated temperature, the sample is removed from the oven and allowed to cool to room temperature (21-23° C.). The position of the glitter particles is again observed and recorded. If the final position of the glitter particles relative to the initial position is ≤5 mm, the sample passes.

The following components are used in the examples of the present technology:

| | Component |
|---|---|
| Cocamidopropyl Betaine | Chembetaine ™ CGF amphoteric surfactant, 35 wt. % active, Lubrizol Advanced Materials, Inc. |
| EA | Ethyl acrylate |
| PPG-20 Methyl Glucose Ether | Glucam ™ P-20 emollient, Lubrizol Advanced Materials, Inc. |
| Ethoxylated Fatty Alcohol Emulsifier | Ethal ® SA-20 Emusifier, $C_{18}$ ethoxylated (20) $C_{18}$ alcohol, Ethox Chemicals |
| MAA | Methacrylic acid |
| MMA | Methyl methacrylate |
| n-BA | n-Butyl acrylate |
| Sodium Laureth Sulfate | Sulfochem ™ ES-2PK anionic ethoxylated surfactant, 27.5 wt. % active, Lubrizol Advanced Materials, Inc. |
| Sodium Lauryl Sulfate | Sulfochem ™ SLS-K anionic surfactant, 30 wt. % active, preserved with methylchloroisothiazolinone (and) methylisothiazolinone, Lubrizol Advanced Materials, Inc. |
| TMPTA | Trimethylolpropane triacrylate |
| C-1 (Carbopol ™ Aqua SF-1 polymer) | INCI Name: Acrylates Copolymer. A cross-linked emulsion copolymer prepared from (meth)acrylic acid and a $C_1$-$C_4$ alkyl ester of (meth)acrylic acid; Supplied as a polymer emulsion with 30 wt. % active solids, Lubrizol Advanced Materials, Inc. |
| C-2 (Carbopol ™ Aqua SF-2 polymer) | INCI Name: Acrylates Crosspolymer-4. A emulsion copolymer prepared from (meth)acrylic acid and a $C_1$-$C_4$ alkyl ester of (meth)acrylic acid, crosslinked with trimethylolpropane triacrylate; Supplied as a polymer emulsion with 30 wt. % active solids, Lubrizol Advanced Materials, Inc. |

Example 1

A polymer was synthesized in a staged, semi-batch, emulsion polymerization to yield a staged gradient latex polymer particle. Into an agitator equipped first reactor containing 146.72 g of deionized (D.I.) water, 10 g of an ethoxylated fatty alcohol emulsifier and 10.67 g of sodium lauryl sulfate (30% active in water wt./wt.), 168.6 g of EA, 200 g of MAA, 1.36 g of TMPTA, and an additional 26.2 g of D.I. water were added under a nitrogen atmosphere and mixed at 900 rpm to form a stable monomer emulsion. To an agitator equipped second reactor, 913.84 g of D.I. water and 1.27 g of sodium lauryl sulfate (30% active in water wt./wt.) were added and mixed under a nitrogen atmosphere at 210 rpm while heating. When the contents of the second reactor reached a temperature of 84° C., 10 g of an ammonium persulfate solution (1.6% aqueous solution wt./wt.) were injected into the heated surfactant solution. The monomer mixture from the first reactor was gradually metered at a feed rate of 3.76 g/min. into the second reactor over a period of 150 minutes at a reaction temperature maintained at approximately 84 to 88° C. With the emulsion monomer feed, 40 g of a 0.25% ammonium persulfate solution (aqueous solution wt./wt.) was simultaneously metered into the reaction mixture in the second reactor over the 150-minute period.

The first stage of the latex particle was allowed to form over a period of 30 minutes following the initiation of the reaction. To prepare for the second stage of the reaction a 60 mL syringe was loaded with a mixture of 1.64 g of TMPTA and 28.40 g of EA. The second stage of the reaction began approximately 30 minutes after the start of first stage polymerization. The reaction temperature was increased to 88° C. while simultaneously beginning the metering of the monomer mixture in the syringe. The second stage monomer mixture was gradually metered into the first reactor at a rate of 0.250 g/min. over a 120-minute time period. The graduated addition of the monomer mixture from the syringe forms the targeted gradient structure of the latex particle. After the completion of the monomer addition, the reaction mixture was held at a temperature of 88° C. for 150 mins. The resulting polymer emulsion product was cooled to room temperature, discharged from the reactor and recovered.

Examples 2 to 16

The polymers of Examples 2 to 16 were polymerized utilizing the same components and conditions as described for the preparation of the polymer of Example 1, except that the amount of the respective monomers was changed as set forth in Table 1. The MFFT for each of the synthesized polymers and commercially available rheology modifying polymers was determined by the testing methodology above. The MFFT results are reported in Table 2.

Example 17

The polymer synthesized in this example was polymerized utilizing the same components and conditions as described for the preparation of the polymers in Example 1 except for how the second stage monomer mixture was added. The second stage monomer mixture was added in multiple batch additions (3 times at 50-minute intervals). After the completion of the monomer addition, the reaction mixture was held at a temperature of 88° C. for 150 mins. The resulting polymer emulsion product was cooled to room temperature, discharged from the reactor and recovered. The MFFT for the polymer was measured and reported in Table 2.

The monomer amounts reported in Table 1 is the total amount of monomer components utilized to prepare the polymer. The monomer amounts reported in Table 1A is the monomer amount utilized to prepare each stage of the polymer.

TABLE 1

| Ex. No. | Total Monomer | | | | Crosslinker Fraction (%) | |
|---|---|---|---|---|---|---|
| | EA | MAA | TMPTA | Sum | First Stage | Second Stage |
| 1 | 49.25 | 50.00 | 0.75 | 100 | 45 | 55 |
| 2 | 49.25 | 50.00 | 0.75 | 100 | 25 | 75 |
| 3 | 49.40 | 50.00 | 0.60 | 100 | 50 | 50 |
| 4 | 49.25 | 49.85 | 0.90 | 100 | 25 | 75 |
| 5 | 49.10 | 50.30 | 0.60 | 100 | 50 | 50 |
| 6 | 49.11 | 49.70 | 1.19 | 100 | 25 | 75 |
| 7 | 49.40 | 50.00 | 0.60 | 100 | 75 | 25 |
| 8 | 49.11 | 49.70 | 1.19 | 100 | 25 | 75 |
| 9 | 49.11 | 49.70 | 1.19 | 100 | 17 | 83 |
| 10 | 49.40 | 50.00 | 0.60 | 100 | 25 | 75 |
| 11 | 49.20 | 49.80 | 1.00 | 100 | 30 | 70 |
| 12 | 49.20 | 50.00 | 0.80 | 100 | 40 | 60 |
| 13[1] | 38.50 | 60.00 | 1.50 | 100 | 25 | 75 |
| 14[1] | 39.25 | 60.00 | 0.75 | 100 | 25 | 75 |
| 15 | 49.25 | 50.00 | 0.75 | 100 | 45 | 55 |
| 16 | 49.25 | 50.00 | 0.75 | 100 | 45 | 55 |
| 17 | 49.25 | 50.00 | 0.75 | 100 | 45 | 55 |

[1]Comparative

TABLE 1A

| Ex. No | First Stage Monomer Composition | | | | Second Stage Monomer Composition | | | |
|---|---|---|---|---|---|---|---|---|
| | EA | MAA | TMPTA | Sum | EA | MAA | TMPTA | Sum |
| 1 | 45.57 | 54.06 | 0.37 | 100 | 50.08 | 49.08 | 0.84 | 100 |
| 2 | 45.65 | 54.15 | 0.21 | 100 | 50.07 | 49.06 | 0.87 | 100 |
| 3 | 45.68 | 54.00 | 0.32 | 100 | 50.20 | 49.04 | 0.76 | 100 |
| 4 | 45.72 | 54.04 | 0.24 | 100 | 50.05 | 48.90 | 1.05 | 100 |
| 5 | 45.33 | 54.35 | 0.33 | 100 | 49.95 | 49.38 | 0.67 | 100 |
| 6 | 45.68 | 54.00 | 0.32 | 100 | 49.88 | 48.73 | 1.39 | 100 |
| 7 | 45.61 | 53.91 | 0.49 | 100 | 50.26 | 49.11 | 0.63 | 100 |
| 8 | 45.68 | 54.00 | 0.32 | 100 | 49.88 | 48.73 | 1.39 | 100 |
| 9 | 45.73 | 54.05 | 0.22 | 100 | 49.87 | 48.72 | 1.41 | 100 |
| 10 | 45.75 | 54.08 | 0.16 | 100 | 50.23 | 49.07 | 0.70 | 100 |
| 11 | 45.68 | 54.00 | 0.32 | 100 | 50.00 | 48.85 | 1.15 | 100 |
| 12 | 45.55 | 54.10 | 0.35 | 100 | 50.03 | 49.07 | 0.90 | 100 |
| 13[1] | 34.21 | 65.37 | 0.41 | 100 | 39.46 | 58.78 | 1.76 | 100 |
| 14[1] | 34.82 | 64.98 | 0.21 | 100 | 40.25 | 58.87 | 0.87 | 100 |
| 15 | 45.57 | 54.06 | 0.37 | 100 | 50.08 | 49.08 | 0.84 | 100 |
| 16 | 45.57 | 54.06 | 0.37 | 100 | 50.08 | 49.08 | 0.84 | 100 |
| 17 | 45.57 | 54.06 | 0.37 | 100 | 50.08 | 49.08 | 0.84 | 100 |

[1]Comparative

TABLE 2

| Ex. No. | Acid Number | Total Solids | MFFT (° C.) |
|---|---|---|---|
| 1 | 320 ± 10 | 25.16 | 25.93 |
| 2 | 320 ± 10 | 30.93 | 25.74 |
| 3 | 320 ± 10 | 25.98 | 24.54 |
| 4 | 320 ± 10 | 27.31 | 21.49 |
| 5 | 320 ± 10 | 31.36 | 24.62 |
| 6 | 320 ± 10 | 31.21 | 23.93 |
| 7 | 320 ± 10 | 30.75 | 36.43 |
| 8 | 320 ± 10 | 36.34 | 25.94 |
| 9 | 320 ± 10 | 26.54 | 25.14 |
| 10 | 320 ± 10 | 25.19 | 25.34 |
| 11 | 320 ± 10 | 25.59 | 25.57 |
| 12 | 320 ± 10 | 25.79 | 24.56 |
| 13[1] | 381.15 | 29.61 | 44.16 |
| 14[1] | 381.15 | 30.29 | 44.41 |
| 15 | 320 ± 10 | 25.54 | 25.78 |
| 16 | 320 ± 10 | 25.22 | 23.88 |
| 17 | 320 ± 10 | 26.00 | 25.33 |
| C-1[1] | 225 ± 10 | 30.0 | 10.80 |
| C-2[1] | 225 ± 10 | 32.0 | 8.10 |

[1]Comparative

Examples 18 to 36

Liquid foamable hand soap compositions were formulated with the polymers of Examples 1 to 17 employing the ingredients set forth in Tables 3 and 3a. In addition, hand soap compositions containing commercially available rheology modifiers C1 and C2 were similarly formulated for comparative purposes (Table 3a).

Formulation Procedure

The foamable hand soap compositions set forth in Tables 3 and 3a were individually prepared as follows:

1) Into a suitable mixing container was added 232 g of D.I. water.
2) The polymer component in the amounts indicated in the table was added to the mixing vessel under gentle mixing with a turbine blade to minimize foam generation.
3) Sodium Lauryl Sulfate, Sodium Laureth Sulfate, Cocamidopropyl Betaine and PPG-20 Methyl Glucose Ether were added to the vessel in the order and amounts listed in the table under continuous gentle mixing.
4) Sodium hydroxide was added in the indicated amount to each soap composition.
5) Additional D.I. water was added to each soap composition to adjust the pH to approximately 6. The soap composition was continuously mixed until homogeneous.

Each of the formulated hand soap compositions were evaluated for viscosity, clarity, yield value and the ability to suspend glitter over an extended period of time. The results of the evaluations are presented in Tables 4 and 4a.

TABLE 3

| | | Ex. No. | | | | | | | | | | |
|---|---|---|---|---|---|---|---|---|---|---|---|---|
| Ingredient | Active wt. % | 18 | 19 | 20 | 21 | 22 | 23 | 24 | 25 | 26 | 27 | 28 |
| | | Ingredient Amount (g) | | | | | | | | | | |
| Polymer Ex. No. | | 1 | 2 | 3 | 4 | 5 | 6 | 7 | 8 | 9 | 10 | 11 |
| Polymer Amount | 1.8 | 28.62 | 23.28 | 27.71 | 26.36 | 22.96 | 23.07 | 23.41 | 27.33 | 27.13 | 28.58 | 28.14 |
| D.I. Water | 58 | 232 | 232 | 232 | 232 | 232 | 232 | 232 | 232 | 232 | 232 | 232 |
| Sodium Lauryl Sulfate | 3 | 41.38 | 41.38 | 41.38 | 41.38 | 41.38 | 41.38 | 41.38 | 41.38 | 41.38 | 41.38 | 41.38 |
| Sodium Laureth Sulfate | 5 | 73.26 | 73.26 | 73.26 | 73.26 | 73.26 | 73.26 | 73.26 | 73.26 | 73.26 | 73.26 | 73.26 |
| Cocamidopropyl Betaine | 1.25 | 14.29 | 14.29 | 14.29 | 14.29 | 14.29 | 14.29 | 14.29 | 14.29 | 14.29 | 14.29 | 14.29 |
| PPG-20 Methyl Glucose Distearate | 0.25 | 1.0 | 1.0 | 1.0 | 1.0 | 1.0 | 1.0 | 1.0 | 1.0 | 1.0 | 1.0 | 1.0 |
| 20% NaOH | q.s. | 3.96 | 3.71 | 3.55 | 2.69 | 3.64 | 3.54 | 3.56 | 3.61 | 3.77 | 4.25 | 4.38 |
| D.I. Water | q.s. | 5.49 | 11.08 | 6.81 | 9.02 | 11.47 | 11.46 | 11.10 | 7.13 | 7.17 | 5.24 | 5.55 |
| Total | 100 | 400 | 400 | 400 | 400 | 400 | 400 | 400 | 400 | 400 | 400 | 400 |

[1]Comparative

TABLE 3a

| | | Ex. No. | | | | | | | |
|---|---|---|---|---|---|---|---|---|---|
| Ingredient | Active wt. % | 29 | 30[1] | 31[1] | 32 | 33 | 34 | 35[1] | 36[1] |
| | | Ingredient Amount (g) | | | | | | | |
| Polymer Ex. No. | | 12 | 13 | 14 | 15 | 16 | 17 | C-1 | C-2 |
| Polymer Amount | 1.8 | 27.92 | 24.32 | 23.77 | 25.54 | 25.22 | 26.0 | 24.24 | 21.69 |
| D.I. Water | 58 | 232 | 232 | 232 | 232 | 232 | 232 | 232 | 232 |
| Sodium Lauryl Sulfate | 3 | 41.38 | 41.38 | 41.38 | 41.38 | 41.38 | 41.38 | 41.38 | 41.38 |
| Sodium Laureth Sulfate | 5 | 73.26 | 73.26 | 73.26 | 72.73 | 72.73 | 72.73 | 73.26 | 73.26 |
| Cocamidopropyl Betaine | 1.25 | 14.29 | 14.29 | 14.29 | 14.29 | 14.29 | 14.29 | 14.29 | 14.29 |
| PPG-20 Methyl Glucose ether | 0.25 | 1.0 | 1.0 | 1.0 | 1.0 | 1.0 | 1.0 | 1.0 | 1.0 |
| 20% NaOH | q.s. | 4.0 | 6.45 | 6.29 | 2.64 | 3.32 | 1.68 | 1.53 | 1.71 |
| D.I. Water | q.s. | 6.15 | 7.33 | 8.01 | 10.42 | 10.06 | 10.92 | 12.30 | 14.67 |
| Total | 100 | 400 | 400 | 400 | 400 | 400 | 400 | 400 | 400 |

[1]Comparative

TABLE 4

| Ex. No. | 18 | 19 | 20 | 21 | 22 | 23 | 24 | 25 | 26 | 27 |
|---|---|---|---|---|---|---|---|---|---|---|
| Polymer No. | 1 | 2 | 3 | 4 | 5 | 6 | 7 | 8 | 9 | 10 |
| pH | 6.0 | 6.0 | 6.01 | 6.0 | 6.0 | 6.0 | 6.0 | 6.0 | 6.0 | 6.0 |

TABLE 4-continued

| Ex. No. | 18 | 19 | 20 | 21 | 22 | 23 | 24 | 25 | 26 | 27 |
|---|---|---|---|---|---|---|---|---|---|---|
| Clarity (NTU) | 18.2 | 17.2 | 17.0 | 33.5 | 16.1 | 37.4 | 37.7 | 50.8 | 35.5 | 28.8 |
| Visc. (mPa · s) ($62^2$@20 rpm) | 1007 | 1032 | 1007 | 1770 | 963 | 954 | 1220 | 892.5 | 1082 | 1037 |
| Visc. (mPa · s) ($62^2$@1.0 rpm) | 7890 | 8010 | 7710 | 15840 | 7170 | 7890 | 10200 | 7140 | 8850 | 7080 |
| Visc. (mPa · s) ($62^2$@0.5 rpm) | 13140 | 13440 | 12840 | 27360 | 12060 | 13740 | 17820 | 12420 | 15300 | 11760 |
| Yield Value (dyn/cm$^2$) | 52.5 | 54.3 | 51.3 | 115.2 | 48.9 | 58.5 | 76.2 | 52.8 | 64.5 | 46.8 |
| Glitter Suspension[3] | Pass | Pass | Pass | Pass | Pass | Pass | Pass | Pass | Pass | Pass |

[2]Spindle size
[3]20 g of the foamable hand soap formulations set forth in Tables 3 and 3a were utilized in the glitter suspension test per the methods protocol.

TABLE 4a

| Ex. No. | 28 | 29 | 30[1] | 31[1] | 32 | 33 | 34 | 35[1] | 36[1] |
|---|---|---|---|---|---|---|---|---|---|
| Polymer No. | 11 | 12 | 13[1] | 14[1] | 15 | 16 | 17 | C-1[1] | C-2[1] |
| pH | 6.01 | 6.0 | 6.01 | 6.0 | 6.03 | 6.07 | 6.1 | 6.0 | 6.04 |
| Clarity (NTU) | 14.4 | 18.4 | 80.5 | 64.0 | 47 | 38.6 | 85.2 | 133.0 | 52.4 |
| Visc. (mPa · s) ($62^2$@20 rpm) | 825 | 1015 | 240 | 800 | 878 | 864 | 465 | 1056 | 560 |
| Visc. (mPa · s) ($62^2$@1.0 rpm) | 6120 | 8070 | 3200 | 6400 | 6450 | 6120 | 3156 | 10560 | 3520 |
| Visc. (mPa · s) ($62^2$@0.5 rpm) | 10140 | 13440 | 3200 | 9600 | 10560 | 10080 | 5148 | 16000 | 4480 |
| Yield Value (dyn/cm$^2$) | 40.2 | 53.7 | 0.0 | 32.0 | 41.1 | 39.6 | 61 | 54.4 | 9.6 |
| Glitter Suspension[3] | Pass | Pass | Fail | Pass | Pass | Pass | Pass | Fail | Fail |

[1]Comparative
[2]Spindle size
[3]20 g of the foamable hand soap formulations set forth in Tables 3 and 3a were utilized in the glitter suspension test per the methods protocol.

Examples 37-52

Liquid foamable hand soap compositions were formulated as set forth in Examples 18-36 except that each composition contained 0.12 wt. % EMD Xirona Magic Mauve mica ($D_{50}$=16.0-22.0 μm). Each of the formulations were transferred into disposable consumer hand soap dispensers equipped with a foam generating dispenser pump (F8T 1.5 cc foam pump 40 mm, #AAF8S15T manufactured by Arminak & Associates; Series: F8S15T, Closure Dimension: 40 mm, Fill Capacity/Output: 1.5 cc). The soap dispensers were placed on an automated pumping apparatus configured with eight pumping stations outfitted with a pneumatic pumping actuator situated directly above the pump for each dispenser. The actuators are designed to continuously depress and release the foam generating dispenser pump. The actuators were connected to a conventional laboratory compressed air supply system equipped with a regulator to control the air pressure at the actuators. A pressure was selected on the regulator that allowed for the complete depression of the dispenser pump. The dispenser pumps were continuously pumped (at two-hour intervals) until the contents of each container were emptied. Visual observations on the quality of dispensing were made as the pumping progressed. Formulations failed if glitter settled in the bottle, if the soap formulation was misdirected as it exited the pump head dispenser orifice, or if a significant amount of polymer accumulated in the pump head dispenser orifice over the duration of the test. The pass/fail results are summarized in Table 5.

TABLE 5

| Example No. | Polymer No. | MFFT (° C.)[2] | Formulation No. | Pass/Fail |
|---|---|---|---|---|
| 37 | 1 | 25.93 | 19 | Pass |
| 38 | 2 | 25.74 | 20 | Pass |
| 39 | 3 | 24.54 | 21 | Pass |
| 40 | 4 | 21.49 | 22 | Pass |
| 41 | 5 | 24.62 | 23 | Pass |
| 42 | 6 | 23.93 | 24 | Pass |
| 43 | 7 | 36.43 | 25 | Pass |
| 44 | 8 | 25.94 | 26 | Pass |
| 45 | 9 | 25.14 | 27 | Pass |
| 46 | 10 | 25.34 | 27 | Pass |
| 47 | 11 | 25.57 | 28 | Pass |
| 48 | 12 | 24.56 | 29 | Pass |
| 49 | 13[1] | 44.16 | 30 | Fail[3] |
| 50 | 14[1] | 44.41 | 31 | Fail[4] |
| 51 | C-1 | 10.80 | 35 | Fail[3] |
| 52 | C-2 | 8.10 | 36 | Fail[3] |

[1]Comparative
[2]MFFT data from Table 2
[3]Failed glitter suspension
[4]Misdirected foam

What is claimed is:

1. Structured emulsion polymer particles comprising:
   (a) from about 15 to about 25 percent by weight of a first stage polymer core which is polymerized from a monomer mixture comprising (i) from about 53 to about 60 weight percent of at least one ethylenically unsaturated $C_3$-$C_6$ carboxylic acid monomer, (ii) from about 39 to about 46 weight percent of at least one $C_1$-$C_4$ alkyl (meth)acrylate monomer, and (iii) at least one crosslinking monomer;
   (b) from about 85 to about 75 percent by weight of a second stage polymer shell which is polymerized from a monomer mixture comprising (i) from about 47 to about 55 weight percent of least one ethylenically unsaturated $C_3$-$C_6$ carboxylic acid monomer, (ii) from about 52 to 44 wt. % of at least one $C_1$-$C_4$ alkyl (meth)acrylate monomer and (iii) at least one crosslinking monomer;

wherein the weight fraction of the at least one ethylenically unsaturated $C_3$-$C_6$ carboxylic acid monomer present in said first stage monomer mixture is 3 to 20 percent greater than the weight fraction of at least one $C_3$-$C_6$ carboxylic acid monomer present in said second stage monomer mixture;

wherein the sum total of said crosslinking monomer present in said first and said second stage monomer mixtures ranges from about 0.5 weight percent to about 1.5 weight percent, based on the weight of the total monomer present in said first and second stage monomer mixtures and the weight fraction of said crosslinking monomer present in said first stage monomer mixture to said second stage monomer mixture ranges from 15:50 to 85:50 percent; and wherein said at least one ethylenically unsaturated $C_3$-$C_6$ carboxylic acid monomer in each of the first stage monomer mixture and the second stage monomer mixture comprises (meth)acrylic acid and said at least one crosslinking monomer in each of the first stage monomer mixture and the second stage monomer mixture comprises a polyfunctional acrylate.

2. The structured emulsion polymer particles of claim 1 wherein said at least one ethylenically unsaturated $C_3$-$C_6$ carboxylic acid monomer in said first stage monomer mixture and in said second stage monomer mixture is independently selected from acrylic acid and methacrylic acid, optionally in combination with itaconic acid, citraconic acid, maleic acid, maleic anhydride, fumaric acid, crotonic acid, aconitic acid, and mixtures thereof.

3. The structured emulsion polymer particles of claim 1 wherein said at least one $C_1$-$C_4$ alkyl (meth)acrylate monomer in said first stage monomer mixture and said second stage monomer mixture is independently selected from methyl (meth)acrylate, ethyl (meth)acrylate, n-butyl (meth)acrylate, t-butyl (meth)acrylate, and mixtures thereof.

4. The structured emulsion polymer particles of claim 1 wherein said at least one ethylenically unsaturated $C_3$-$C_6$ carboxylic acid monomer in said first stage monomer mixture is methacrylic acid.

5. The structured emulsion polymer particles of claim 1 wherein said at least one ethylenically unsaturated $C_3$-$C_6$ carboxylic acid monomer in said second stage monomer mixture is methacrylic acid.

6. The structured emulsion polymer particles of claim 1 wherein said at least one $C_1$-$C_4$ alkyl (meth)acrylate monomer in said first stage monomer mixture is selected from ethyl acrylate, butyl acrylate, and mixtures thereof.

7. The structured emulsion polymer particles of claim 1 wherein said at least one $C_1$-$C_4$ alkyl (meth)acrylate monomer in said second stage monomer mixture is selected from ethyl acrylate, butyl acrylate, and mixtures thereof.

8. The structured emulsion polymer particles of claim 1 wherein said crosslinking monomer in said first stage monomer mixture and said second stage monomer mixture is independently selected from a polyfunctional acrylate optionally in combination with a polyallyl ether.

9. The structured emulsion polymer particles of claim 8 wherein said crosslinking monomer is selected from ethylene glycol di(meth)acrylate, triethylene glycol di(meth)acrylate, 1,3-butylene glycol di(meth)acrylate, 1,4-butylene glycol di(meth)acrylate, 1,6-hexanediol di(meth)acrylate, neopentyl glycol di(meth)acrylate, 1,9-nonanediol di(meth)acrylate, trimethylolpropane tri(meth)acrylate, trimethylolethane tri(meth)acrylate, tetramethylolmethane tri(meth)acrylate, ditrimethylolpropane tetra(meth)acrylate, tetramethylolmethane tetra(meth)acrylate, pentaerythritol tetra(meth)acrylate; dipentaerythritol hexa(meth)acrylate, 1,4-cyclohexanediol dimethacrylate, and mixtures thereof.

10. The structured emulsion polymer particles of claim 8 wherein said crosslinking monomer is selected from allyl (meth)acrylate.

11. The structured emulsion polymer particles of claim 9 wherein said crosslinking monomer in said first stage monomer mixture and said second stage monomer mixture is selected from trimethylolpropane triacrylate.

12. The structured emulsion polymer particles of claim 1 having a minimum film formation temperature ranging from about 18 to about 40° C.

13. A thickener comprising the structured emulsion polymer particles of claim 1.

14. A cleansing composition comprising:
(a) from about 0.5 to about 40 wt. % of at least one foaming surfactant;
(b) from about 0.05 wt. % to about 10 wt. % of the polymer (active polymer solids) of claim 1; and
(c) water, wherein weight percentages are based on the total weight of the composition.

15. The cleansing composition of claim 14 further comprising an alkaline neutralizing agent.

16. The cleansing composition of claim 14 further comprising suspended particles.

17. The cleansing composition claim 14 having a Brookfield viscosity ranging from about 300 to about 1000 mPa·s at 25° C.

18. The cleansing composition of claim 14 having a yield value of ≥12 dyn/cm².

19. The cleansing composition of claim 14, wherein said at least one foaming surfactant is selected from an anionic surfactant, an amphoteric surfactant, zwitterionic surfactant, cationic surfactant, nonionic surfactant, and mixtures thereof.

20. The cleansing composition of claim 14 wherein said at least one surfactant is a mixture of an anionic surfactant and an amphoteric surfactant.

21. The cleansing composition of claim 20 wherein the weight ratio of anionic surfactant to amphoteric surfactant (active material) is 10:1 to about 2:1.

22. The cleansing composition of claim 16 wherein said particles are selected from coated mica, mica coated metal oxides, pigments, exfoliants, anti-dandruff agents, clay, swellable clay, laponite, gas bubbles, liposomes, microsponges, cosmetic beads, flakes and glitter.

23. A process for preparing a structured emulsion polymer formed by sequentially polymerizing from about 15 to about 25 wt. % of a first monomer mixture to form a core and from about 85 to about 75 wt. % of a second monomer mixture to form a shell, wherein said first monomer mixture comprises (i) from about 53 to about 60 weight percent of at least one ethylenically unsaturated $C_3$-$C_6$ carboxylic acid monomer, (ii) from about 39 to about 46 weight percent of at least one $C_1$-$C_4$ alkyl (meth)acrylate monomer, and (iii) at least one crosslinking monomer; and said second monomer mixture comprises (iv) from about 47 to about 55 weight percent of least one ethylenically unsaturated $C_3$-$C_6$ carboxylic acid monomer (v) from about 52 to 44 wt. % of at least one $C_1$-$C_4$ alkyl (meth)acrylate monomer, and (vi) at least one crosslinking monomer;

wherein the weight fraction of the at least one $C_3$-$C_6$ carboxylic acid monomer present in said first monomer mixture is 3 to 20 percent greater than the weight fraction of the at least one $C_3$-$C_6$ carboxylic acid monomer present in said second monomer mixture;

wherein the sum total of said crosslinking monomer present in said first and said second monomer mixtures ranges from about 0.5 weight percent to about 1.5 weight percent (based on the weight of the total monomer present in said first and second monomer mixtures) and the weight fraction of said crosslinking monomer present in said first monomer mixture to said second monomer mixture ranges from 15:50 to 85:50 percent; and wherein said at least one ethylenically unsaturated $C_3$-$C_6$ carboxylic acid monomer in each of the first stage monomer mixture and the second stage monomer mixture comprises (meth)acrylic acid and said at least one crosslinking monomer in each of the first stage monomer mixture and the second stage monomer mixture comprises a polyfunctional acrylate.

* * * * *